US011583647B2

(12) United States Patent
Zhou et al.

(10) Patent No.: US 11,583,647 B2
(45) Date of Patent: Feb. 21, 2023

(54) MULTI-CHANNEL FLEXIBLE LARYNGEAL MASK AIRWAY DEVICE

(71) Applicant: Gary Zhou, Guilford, CT (US)

(72) Inventors: Gary Zhou, Guilford, CT (US); Juan Li, Hefei (CN); Tianzuo Li, Beijing (CN); Wenxian Li, Shanghai (CN)

(73) Assignee: Gary Zhou, Guilford, CT (US)

( * ) Notice: Subject to any disclaimer, the term of this patent is extended or adjusted under 35 U.S.C. 154(b) by 869 days.

(21) Appl. No.: 16/280,107

(22) Filed: Feb. 20, 2019

(65) Prior Publication Data

US 2020/0261676 A1  Aug. 20, 2020

(51) Int. Cl.
*A61M 16/04* (2006.01)
*A61B 1/267* (2006.01)
*A61M 25/02* (2006.01)
*A61M 25/00* (2006.01)
*A61M 27/00* (2006.01)

(52) U.S. Cl.
CPC ......... *A61M 16/0415* (2014.02); *A61B 1/267* (2013.01); *A61M 16/0409* (2014.02); *A61M 16/0447* (2014.02); *A61M 16/0463* (2013.01); *A61M 16/0477* (2014.02); *A61M 25/02* (2013.01); *A61M 25/0071* (2013.01); *A61M 27/00* (2013.01); *A61M 2025/0076* (2013.01)

(58) Field of Classification Search
CPC .......... A61M 16/0415; A61M 16/0409; A61M 16/0447; A61M 16/0463; A61M 16/0477; A61M 25/02; A61M 25/0071; A61M 27/00; A61M 2025/0076; A61M 25/0026; A61M 25/005; A61M 25/0068; A61M 25/007; A61M 25/04; A61M 31/00; A61M 2205/583; A61M 16/0486; A61M 16/0402; A61B 1/267

See application file for complete search history.

(56) References Cited

U.S. PATENT DOCUMENTS 4,762,125 A * 8/1988 Leiman .................. A61M 1/84
128/207.15
5,241,956 A 9/1993 Brain
(Continued)

FOREIGN PATENT DOCUMENTS

CN  201823142 U  5/2011
CN  102120056 A  7/2011
(Continued)

OTHER PUBLICATIONS

Zhou, Gary X., "Laryngeal Mask Airway Embedded With Pharyngeal Suction Catheters for Rhinoplasty: A Case Report." A A Pract. Jan. 1, 2018; 1 0(1): 13-15. doi: 1 0.1213/XAA.0000000000000622.; retrieved from https://journals.ww.com/aacr/fulltextl/2018/01010/Laryngeal_Mask_Airway_Embedded_With_Pharyngeal.4.aspx.
(Continued)

*Primary Examiner* — Colin W Stuart
*Assistant Examiner* — Matthew D Ziegler
(74) *Attorney, Agent, or Firm* — McCarter & English, LLP

(57) ABSTRACT

Airway devices, systems, and methods are provided that can achieve ventilation of lungs through a mask that seals around the glottis and connects to a flexible airway channel, while also providing evacuation of gastric and/or pharyngeal body fluid and/or blood during upper airway surgeries or procedures.

34 Claims, 33 Drawing Sheets

(56) References Cited

U.S. PATENT DOCUMENTS

| | | | |
|---|---|---|---|
| 5,305,740 A | 4/1994 | Kolobow | |
| 5,315,992 A | 5/1994 | Dalton | |
| 5,632,271 A * | 5/1997 | Brain | A61M 16/04 128/207.15 |
| 5,682,880 A * | 11/1997 | Brain | A61M 16/0488 128/207.15 |
| 6,443,156 B1 | 9/2002 | Niklason et al. | |
| 6,631,720 B1 * | 10/2003 | Brain | A61M 16/0486 128/207.14 |
| 7,013,899 B2 | 3/2006 | Alfery et al. | |
| 7,159,589 B2 * | 1/2007 | Brain | A61M 16/0415 128/207.14 |
| 7,174,889 B2 * | 2/2007 | Boedeker | A61M 16/04 128/200.26 |
| 7,997,274 B2 | 8/2011 | Baska | |
| 8,757,159 B2 | 6/2014 | Nierich | |
| 9,357,905 B2 | 6/2016 | Molnar et al. | |
| 9,744,323 B2 | 8/2017 | Hoftman et al. | |
| 9,839,755 B2 * | 12/2017 | Pacey | A61M 16/0434 |
| 9,956,367 B1 | 5/2018 | Sun | |
| 10,441,735 B1 | 10/2019 | Zhou | |
| 2003/0040678 A1 | 2/2003 | Robinson | |
| 2004/0144387 A1 | 7/2004 | Amar | |
| 2007/0017527 A1 | 1/2007 | Totz | |
| 2008/0071249 A1 | 3/2008 | Vadivelu | |
| 2008/0276936 A1 | 11/2008 | Cook | |
| 2009/0000622 A1 | 1/2009 | Murray | |
| 2011/0023890 A1 | 2/2011 | Baska | |
| 2011/0220117 A1 | 9/2011 | Dubach | |
| 2012/0048279 A1 | 3/2012 | Brain | |
| 2013/0186407 A1 | 7/2013 | Hammer | |
| 2013/0220332 A1 | 8/2013 | Baska et al. | |
| 2013/0269689 A1 | 10/2013 | Brain | |
| 2013/0324798 A1 | 12/2013 | Molnar et al. | |
| 2014/0000624 A1 | 1/2014 | Miller | |
| 2014/0128672 A1 | 5/2014 | Daher et al. | |
| 2014/0150782 A1 | 6/2014 | Vazales et al. | |
| 2014/0309494 A1 | 10/2014 | Molnar | |
| 2014/0323806 A1 | 10/2014 | Brain | |
| 2015/0007826 A1 | 1/2015 | Chaudhry | |
| 2015/0122251 A1 | 5/2015 | Azhir et al. | |
| 2015/0151063 A1 | 6/2015 | Hoftman et al. | |
| 2016/0038014 A1 | 2/2016 | Molnar | |
| 2016/0114117 A1 | 4/2016 | Cook | |
| 2016/0206841 A1 | 7/2016 | Vadivelu | |
| 2016/0243326 A1 | 8/2016 | Hammer et al. | |
| 2017/0065782 A1 * | 3/2017 | Acha Gandarias | A61M 16/0415 |
| 2017/0216544 A1 | 8/2017 | Baska | |
| 2018/0228991 A1 | 8/2018 | Cook | |
| 2020/0001032 A1 | 1/2020 | Zhou et al. | |

FOREIGN PATENT DOCUMENTS

| | | |
|---|---|---|
| CN | 205215883 U | 5/2016 |
| CN | 105214188 B | 7/2017 |
| JP | 4424902 B2 | 3/2010 |
| WO | 2009025843 A1 | 2/2009 |
| WO | 2017080347 A1 | 5/2017 |
| WO | 2021050873 A1 | 3/2021 |

OTHER PUBLICATIONS

International Search Report and Written Opinion from related International Patent Application No. PCT/US2020/018748 dated May 22, 2020.

International Search Report and Written Opinion from related International Patent Application No. PCT/US2019/031323 dated Jun. 13, 2019.

International Search Report and Written Opinion from related International Patent Application No. PCT/JS2020/050405 dated Feb. 16, 2021.

Supplementary European Search Report for Application No. 19799959.2, dated Jan. 4, 2022, 9 pages.

* cited by examiner

Section 1-1

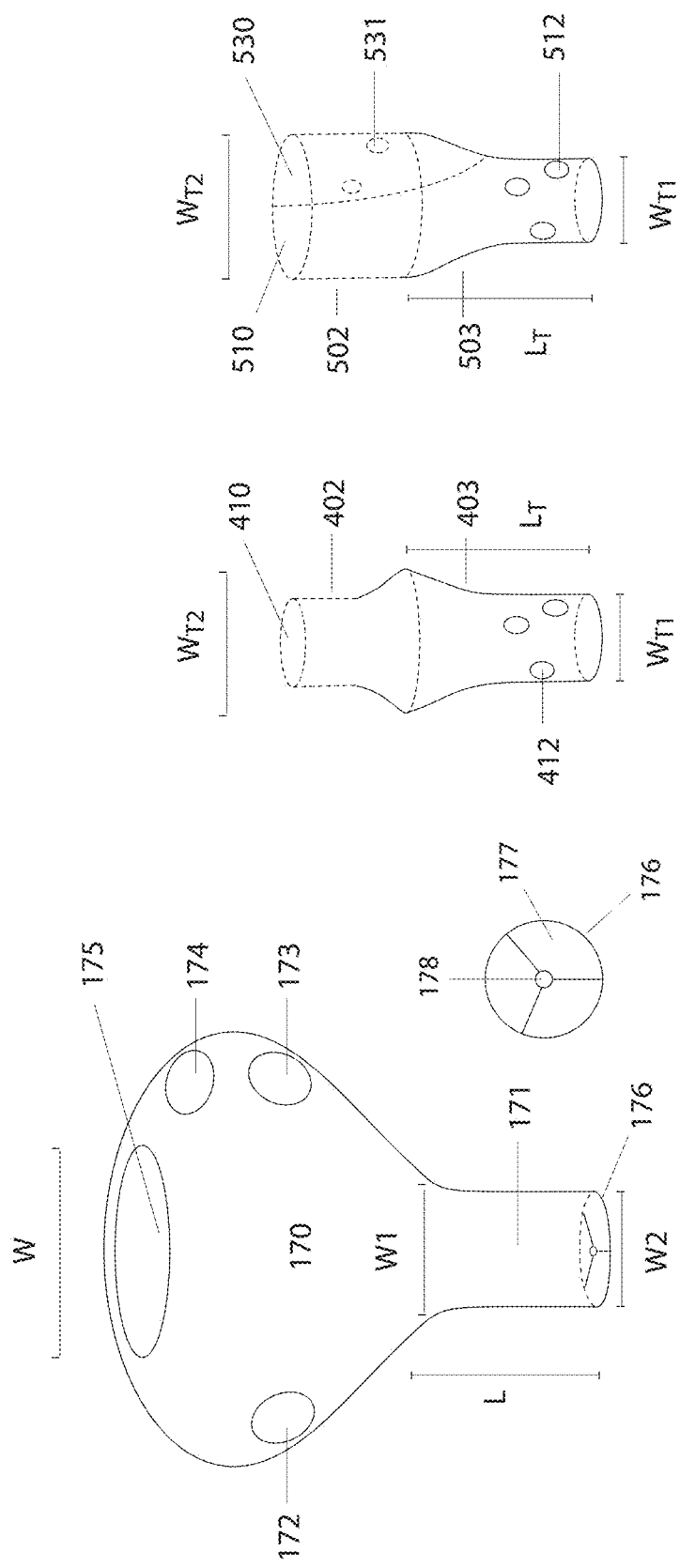

MULTI-CHANNEL FLEXIBLE LARYNGEAL MASK AIRWAY DEVICE

TECHNICAL FIELD

The present disclosure relates to a multi-channel airway device for surgeries and procedures involving the human upper airway.

BACKGROUND

Use of laryngeal mask airway devices for upper airway surgeries has been accepted as an alternative to the use of endotracheal tubes. A reinforced flexible laryngeal mask is generally preferred because its flexible, longer and thinner airway channel offers better access to the surgical field than other types of laryngeal mask. When placed properly, a laryngeal mask covers the glottis and protects the glottis and subglottic area from contamination with blood or other fluids that accumulates in the pharynx during upper airway surgery. However, the glottic seal formed by the mask is variable and dynamic, depending on numerous factors. As a result, aspiration due to leaking of blood or other fluids into the glottic area and the trachea has been reported in cases of laryngeal mask use during upper airway surgeries. In addition, the flexible laryngeal mask, like other first-generation laryngeal masks, typically does not prevent gastric insufflation during positive pressure ventilation, which is generally believed to lead to a higher risk of aspiration of gastric contents and subsequent complications. As a result, safety concerns surrounding the application of flexible laryngeal masks in upper airway surgeries persist in general. Furthermore, leaking of blood into the stomach may cause gastric irritation and possible increased incidence of postoperative nausea and vomiting.

SUMMARY

Exemplary embodiments of the present disclosure relate to airway devices, systems, and associated methods. Embodiments of the airway devices, systems, and methods can achieve ventilation of lungs through a mask that seals around the glottis and connects to a flexible airway channel, while also providing evacuation of gastric and/or pharyngeal body fluid and/or blood through a channel-ampulla-drain system integrated with the mask during upper airway surgeries or procedures. Exemplary embodiments of the present disclosure can improve the safety of airway management and lung ventilation for upper airway surgeries. For example, embodiments of the present disclosure can minimize the risk of aspiration of blood or other fluid accumulated in the pharynx as well as the risk of aspiration of gastric contents during upper airway surgeries.

In accordance with embodiments of the present disclosure, a laryngeal mask airway system is disclosed. The system includes an airway channel portion including an airway channel and a mask portion operatively coupled to the airway channel portion via an airway channel-mask junction. The mask portion includes a mask and an ampulla. The ampulla is disposed at a distal end of the mask portion and includes ports. The mask portion can also include a pharyngeal suction channel and/or a gastric-pharyngeal access channel. For embodiments that include the pharyngeal suction channel, the pharyngeal suction channel can extend through the mask portion from the airway channel-mask junction and terminate at one of the upper ports the ampulla. For embodiments that include the gastric-pharyngeal access channel, the gastric-pharyngeal access channel originates with an opening at a proximal end of the mask portion in proximity to the airway channel-mask junction and terminates at one of the upper ports of the ampulla. A ramp can be formed on the mask that slopes towards the opening of the gastric-pharyngeal access channel. The gastric-pharyngeal access channel can have an oval cross-sectional shape.

A lower port of the ampulla can be opposingly spaced from the upper port associated with the gastric-pharyngeal access channel and can open towards an esophagus of a human when the mask portion is placed in the hypopharynx of the human. This lower port can have a funnel-shape with first cross-sectional dimensions at the ampulla and second cross-sectional dimensions at a distal end of the lower port. A first cross-sectional area of the lower port at the ampulla is greater than the second cross-sectional area of the lower port at the distal end of the lower port. The distal end of the lower port can include a valve, which can be formed by a plurality of leaflets. In a closed position, adjacent ones of the plurality of leaflets of the valve engage each other to form a center opening. The gastric-pharyngeal access channel can have a third cross-sectional area that is greater than the cross-sectional area of the lower port opposing the upper port connected to the gastric-pharyngeal access channel.

In accordance with embodiments of the present disclosure, the system can include at least one pharyngeal drain formed on the mask. The at least one pharyngeal drain can be operatively coupled to one of the ports of the ampulla. For embodiments, that include a second pharyngeal drain, the second pharyngeal drain can be operatively coupled to another one of the ports of the ampulla.

In accordance with embodiments of the present disclosure, the system can include a pharyngeal suction channel that extends from a proximal end of the airway channel portion to the fourth port of the ampulla. A first portion of the pharyngeal suction channel can be formed within or outside of the airway channel and a second portion of the pharyngeal suction channel can be formed within the mask. The first portion of the pharyngeal suction channel can be formed by a suction catheter. For embodiments in which the first portion of the of the pharyngeal suction channel is formed outside the airway channel, the first portion can be attached to the airway channel portion or separate from the airway channel.

In accordance with embodiments of the present disclosure, the system can include a dual suction tube having a lower section, an upper section, and a transitional zone between the lower and upper sections. The lower section can include at least one eyelet disposed at a distal end of the lower section. The upper section can include at least one port configured to be connect to a vacuum source. The transitional zone can be disposed between the lower and upper section. The transitional zone can have a first cross-sectional area proximate the proximal end of the transitional zone and a second cross-sectional area proximate to the distal end of the transitional zone, wherein the first cross-sectional area is greater than the second cross-sectional area such that proximal end of the transitional zone is larger than a distal end of the transitional zone. The transitional zone can include at least one eyelet, which can be disposed proximate to the distal end of the transitional zone.

The lower section of the dual suction tube can be configured and dimensioned to be inserted in and passed through the gastric-pharyngeal access channel, the upper port connecting the gastric-pharyngeal access channel to the ampulla, the ampulla, and the lower port opposingly spaced from the upper port. The upper section and/or the transitional zone can be configured and dimensioned to be inserted in and passed through the gastric-pharyngeal access channel, the upper port connecting the gastric-pharyngeal access channel to the ampulla, and the ampulla, however, the transitional zone can be configured and dimensioned to engage, or to be inserted in but not to be passed through, the lower port of the ampulla because the distal part of the lower port can be dimensioned to prevent the transitional zone from passing through. The dual suction tube can be configured and/or dimensioned to be inserted into the mask portion via the gastric-pharyngeal channel until the transitional zone engages the lower port of the ampulla and stops the advancement of the dual suction tube.

The at least one eyelet disposed near the distal end of the transitional zone can be blocked when the transitional zone is engaged with the lower port of the ampulla. The dual suction tube can include an inner (air) lumen that forms an air vent and a gastric lumen. In some embodiments, the dual suction tube can include a pharyngeal lumen. The gastric lumen extends a length of the dual suction tube. The inner lumen can be disposed within the gastric lumen.

In accordance with embodiments of the present disclosure, for embodiments that include the pharyngeal lumen, the pharyngeal lumen can extend from a proximal end of the dual suction tube to the transitional zone. The pharyngeal lumen can include at least one eyelet disposed at a distal end of the pharyngeal lumen which is configured to be positioned in the ampulla when the dual suction tube is inserted into the mask portion. The dual suction tube can have an oval cross-section shape in the upper section that is defined by the gastric lumen and the pharyngeal lumen and can have a circular cross-sectional shape in the lower section defined by the gastric lumen. The pharyngeal lumen has at least one eyelet, which can be disposed in the pharyngeal lumen proximate a distal end of the pharyngeal lumen. The gastric lumen and the pharyngeal lumen can each have a port at the proximal end of the dual suction tube, wherein each port is configured to be connected to a separate vacuum source.

In accordance with embodiments of the present disclosure, the dual suction tube can be configured to be withdrawn a specified distance from the mask portion to align the at least one eyelet of the transitional zone with the ampulla to place the eyelet of the transitional zone of the dual suction tube in fluid communication with the ampulla.

Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 9B illustrates a cross-sectional view of an upper section of the exemplary DST through line 2-2 in FIG. 9A according to embodiments of the present disclosure.

FIG. 9C illustrates a cross-sectional view of a lower section of the exemplary DST through line 3-3 in FIG. 9A according to embodiments of the present disclosure.

FIG. 10 illustrates an exemplary ampulla in accordance with embodiments of the present disclosure.

FIGS. 11A and 11B illustrate exemplarily a transitional zone of an embodiment of the DST of FIGS. 8A-B and a transitional zone of an embodiment of the DST of FIGS. 9A-C, respectively, in accordance with embodiments of the present disclosure.

DETAILED DESCRIPTION

Exemplary embodiments of the present disclosure relate to airway devices, systems, and methods that can achieve ventilation of lungs through a mask that seals around the glottis and connects to a flexible airway channel, while also providing evacuation of gastric and/or pharyngeal body fluid and/or blood during upper airway surgeries or procedures. Exemplary embodiments of the present disclosure can improve the safety of airway management and lung ventilation for upper airway surgeries. For example, embodiments of the present disclosure can minimize the risk of aspiration of blood or other fluid accumulated in the pharynx as well as the risk of aspiration of gastric contents during upper airway surgeries.

Figure 1A:
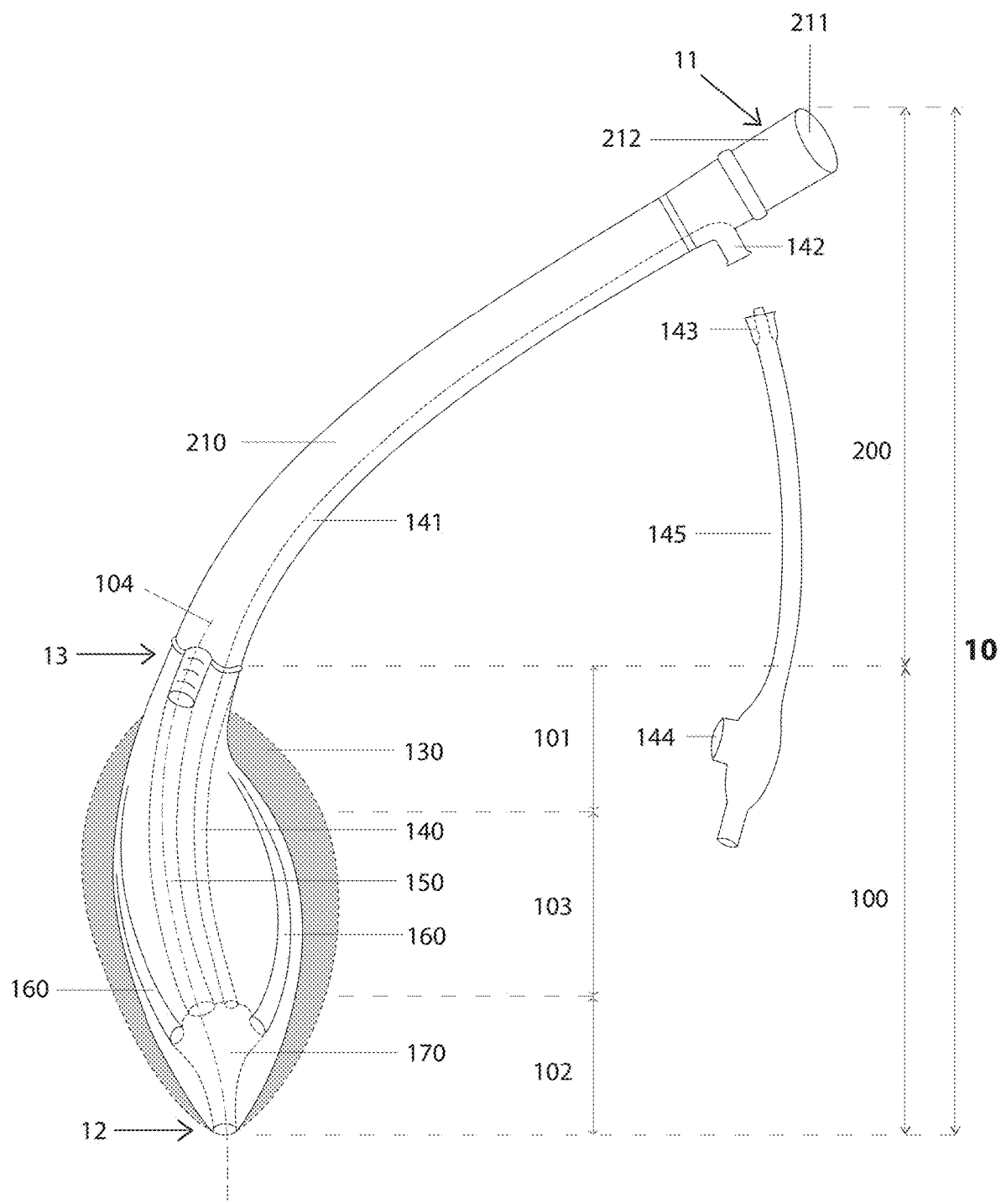
FIGS. 1A and 1B illustrate perspective views of exemplary multi-channel flexible laryngeal mask airway devices having a combined gastric-pharyngeal access channel and a pharyngeal suction channel disposed inside and outside of an airway channel, respectively, according to embodiments of the present disclosure.
Figure 1B:
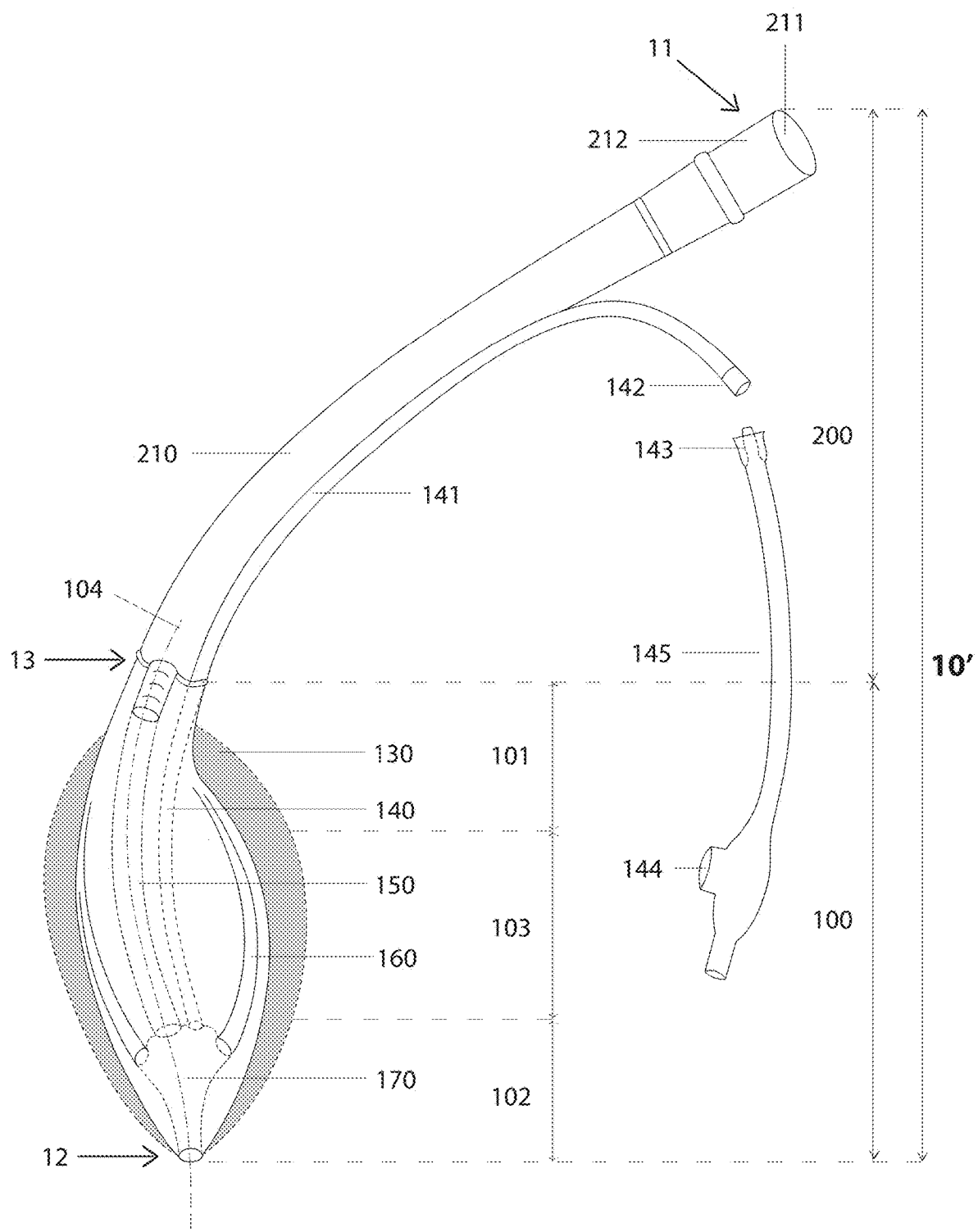

FIGS. 1A-B illustrate a perspective view of exemplary multi-channel flexible laryngeal mask airway devices 10 and 10', respectively, according to embodiments of the present disclosure. The airway devices 10 and 10' can include a mask portion 100 and an airway channel portion 200. The mask portion 100 can define a distal end 12 of the airway devices 10 and 10'. The airway channel portion 200 can extend from the mask portion 100 and can have a free terminal end that forms a proximal end 11 of the airway devices 10 and 10'. For example, the airway channel portion 200 can extend from the proximal end 11 of the airway devices 10 and 10' to the mask portion 100 and can terminate at a mask-airway channel junction 13 near a base 101 of the mask 110.

The mask portion 100 can include a mask 110 defined as a pear-shaped, dome-like structure having the base 101, an apex 102, and a torso 103 disposed between the base 101 and the apex 102. The mask 110 can be dimensioned and configured to fit within the upper airway of a human to cover and/or seal around the glottis of the human. The dome-like structure of the mask 110 can form a convex surface for a posterior side of the mask 110 which faces towards a posterior pharynx of a human when the mask portion 100 is positioned in the hypopharynx and can form a generally concave surface for an anterior side of the mask 110 which faces towards a larynx or glottis of a human when the mask portion 100 is positioned in the hypopharynx. The mask portion 100 can include a membrane cuff or other cushion material 130 that surrounds a perimeter of the mask 110. The mask portion 100 can extend along a centerline 104 from a first end defined by the mask-airway channel junction 13 to a second end defined by the distal end 12 of the mask portion 100. The first or proximal end of the mask portion 100 can be connected to or integrally formed with the airway channel portion 200 and can include an opening that is in fluid communication with an interior volume of an airway channel 210 of the airway channel portion 200 to form the mask-airway channel junction 13. The first or proximal end of the mask portion 100 can be oriented towards a mouth of a human when the mask portion 100 is positioned in the hypopharynx. The second or distal end of the mask portion, which forms the distal end 12 of the airway device 10 or 10', can be oriented towards an esophagus of a human when the mask portion 100 is positioned within the hypopharynx. In exemplary embodiments, the mask portion 100 can include a pharyngeal suction channel 140, a gastric-pharyngeal (or gastropharyngeal) access channel 150, pharyngeal drains 160, and an ampulla 170 as described herein. The pharyngeal suction channel 140, the gastric-pharyngeal access channel 150, the pharyngeal drains 160, and the ampulla 170 can be formed on and/or embedded within the mask 110.

The airway channel portion 200 extends from the proximal end 11 to the mask-airway channel junction 13 and can include the airway channel 210. The proximal end 11 of the airway devices 10 and 10' includes an opening 211 to the interior volume of the airway channel 210. The second or distal end of the airway channel 210 connects to or is integrally formed with the mask 110 of the mask portion 100 at the mask-airway channel junction 13. The airway channel 210 can be a flexible tubular structure that is reinforced with wires. For example, the airway channel 210 can include an embedded coil wire extending a length of the airway channel 210 such that the airway channel 210 is flexible, but provides resistance to radially inward deformation of the airway channel 210. In exemplary embodiments, the airway channel 210 can have an internal diameter of approximately 5 millimeters to approximately 11 millimeters or approximately 7 millimeters to approximately 9 millimeters with a length of approximately 18 centimeters to approximately 30 centimeters or approximately 22 centimeters to approximately 26 centimeters for adults. In exemplary embodiments, the airway channel 210 can have an internal diameter of approximately 4 millimeters to approximately 7 millimeters or approximately 4.5 millimeters to approximately 6.5 millimeters with a length of approximately 14 centimeters to approximately 21 centimeters or approximately 15 centimeters to approximately 20 centimeters for children.

As shown in FIGS. 1A and 1B, the pharyngeal suction channel 140 can extend from the ampulla 170 towards the proximal end 11 of the airway device 10 or 10'. At the mask-airway channel junction 13, the pharyngeal suction channel 140 can continue upward as a non-rigid pharyngeal suction catheter 141. As shown in FIG. 1A, the pharyngeal suction catheter 141 can be disposed within the interior volume of the airway channel 210 and can terminate as a port formed near the proximal end 11 of the airway device 10. For example, the pharyngeal suction channel 140 and catheter 141 can terminate as a female luer lock connector 142, which may be connected to an extension catheter 145. The pharyngeal suction catheter 141 inside the airway channel 210 exits the airway channel as the female luer lock connector 142 below an airway connector 212 near the proximal end 11 of the airway channel 210. As shown in FIG. 1B, the pharyngeal suction catheter 141 can be disposed outside of and along a length of the flexible airway channel 210 of the airway device 10'. The pharyngeal suction catheter 141 in airway device 10' can be attached to the outside of the airway channel 210 or can be free from the airway channel 210, and terminates as the free female luer lock connector 142. The female luer lock connector 142 of the airway devices 10 and 10' can be connected to a male luer lock connector 143 of an extension catheter 145 (FIG. 1A) to direct the pharyngeal suction away from the surgical field and close to the anesthetist. The extension catheter 145 can terminate as a three-way port 144 to prevent accidental continuous suction, which may cause injury to the airway mucosa. The pharyngeal suction channel 140 and catheter 141 may be flushed with a syringe through the female luer lock connector 142.

As shown in FIGS. 1A and 1B, in one embodiment, the gastric-pharyngeal access channel 150 can extend along the spine or centerline 104 of the mask 110 from the ampulla 170 to mask-airway channel junction 13, and the pharyngeal suction channel 140 can be offset to one side of the spine or centerline 104 of the mask 110. The pharyngeal suction channel 140 and the gastric-pharyngeal access channel 150 extend generally parallel to each other in the mask portion 100 of the airway devices 10 and 10' from the ampulla to the mask-airway channel junction 13 or the pharyngeal suction channel 140 can extend at angle relative to the gastric-pharyngeal access channel such that the pharyngeal suction channel 140 and the gastric-pharyngeal access channel 150 converge at the ampulla and diverge at the mask-airway channel junction 13.

In an exemplary application, the airway device 10 or 10' can be inserted into the upper airway of a human such that the mask portion 100 is positioned in the hypopharynx of the human and the airway channel portion 200 extends from the mask portion such that the free terminal end of the airway channel 210 (i.e., the proximal end 11 of the airway device 10 or 10') is positioned outside of a mouth of the human. When the airway device 10 or 10' is positioned in the upper airway of the human, the airway device 10 or 10' can allow access to the upper airway of the human for surgeries or procedures involving the upper airway. When the airway device 10 or 10' is positioned in the upper airway of the human, the airway device 10 or 10' can facilitate ventilation of lungs through the mask 110 and the flexible thin airway channel 210, while also providing evacuation of gastric and/or pharyngeal body fluid and/or blood during upper airway surgeries or procedures through two evacuation systems embedded in and integrated with the airway device, that is, through a first evacuation system formed by the gastric-pharyngeal access channel 150, the pharyngeal drains 160, and the ampulla 170, and a second evacuation system formed by the pharyngeal suction channel 140, the pharyngeal drains 160, and the ampulla 170. Therefore, the airway devices 10 and 10' can improve the safety of airway management and lung ventilation for upper airway surgeries, for example, by minimizing the risk of aspiration of blood or other fluid accumulated in the pharynx as well as minimizing the risk of aspiration of gastric contents.

Figure 2A:
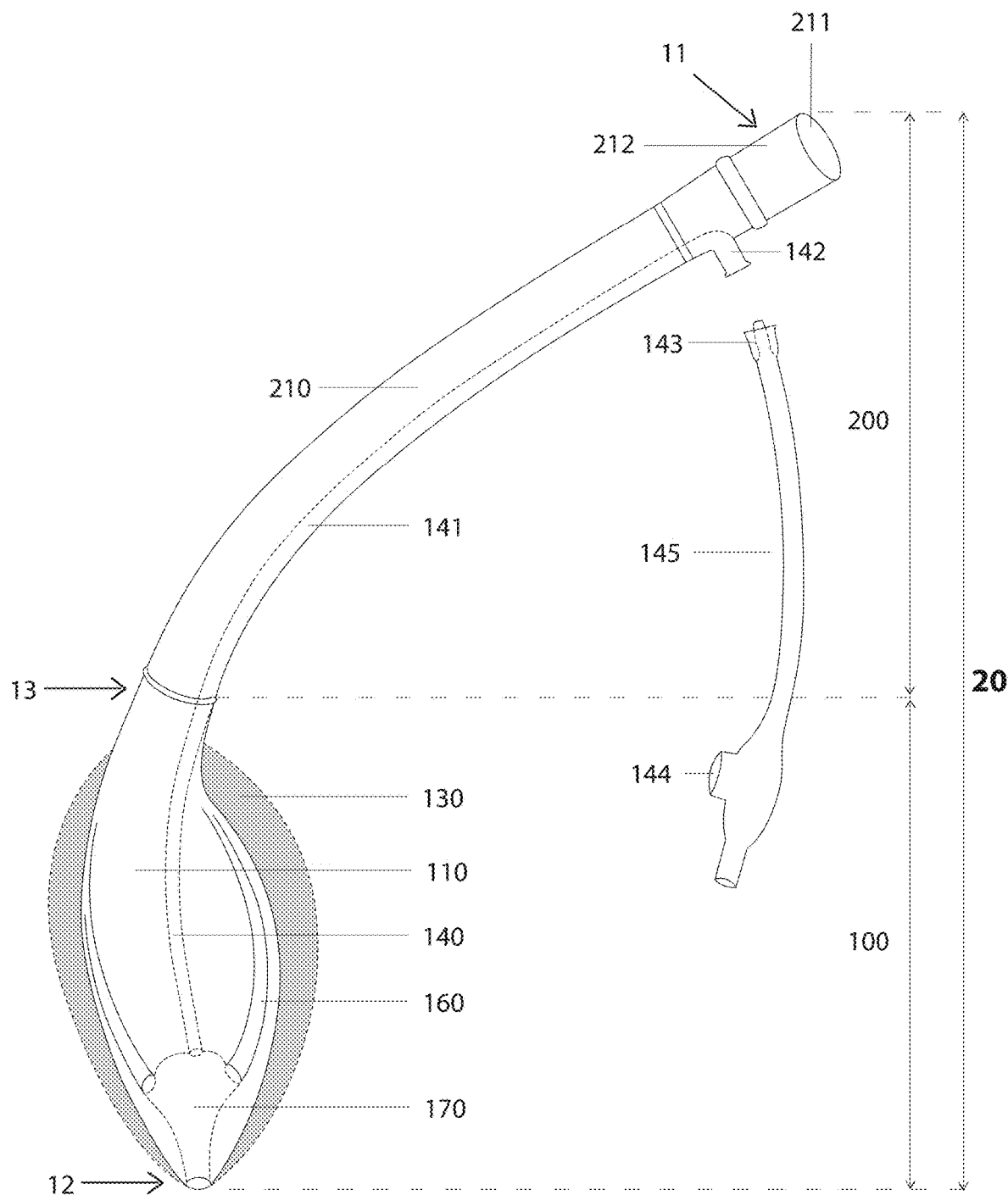
FIGS. 2A and 2B illustrate perspective views of exemplary multi-channel flexible laryngeal mask airway devices having a pharyngeal suction channel disposed within an airway channel and outside of an airway channel, respectively, according to embodiments of the present disclosure.
Figure 2B:
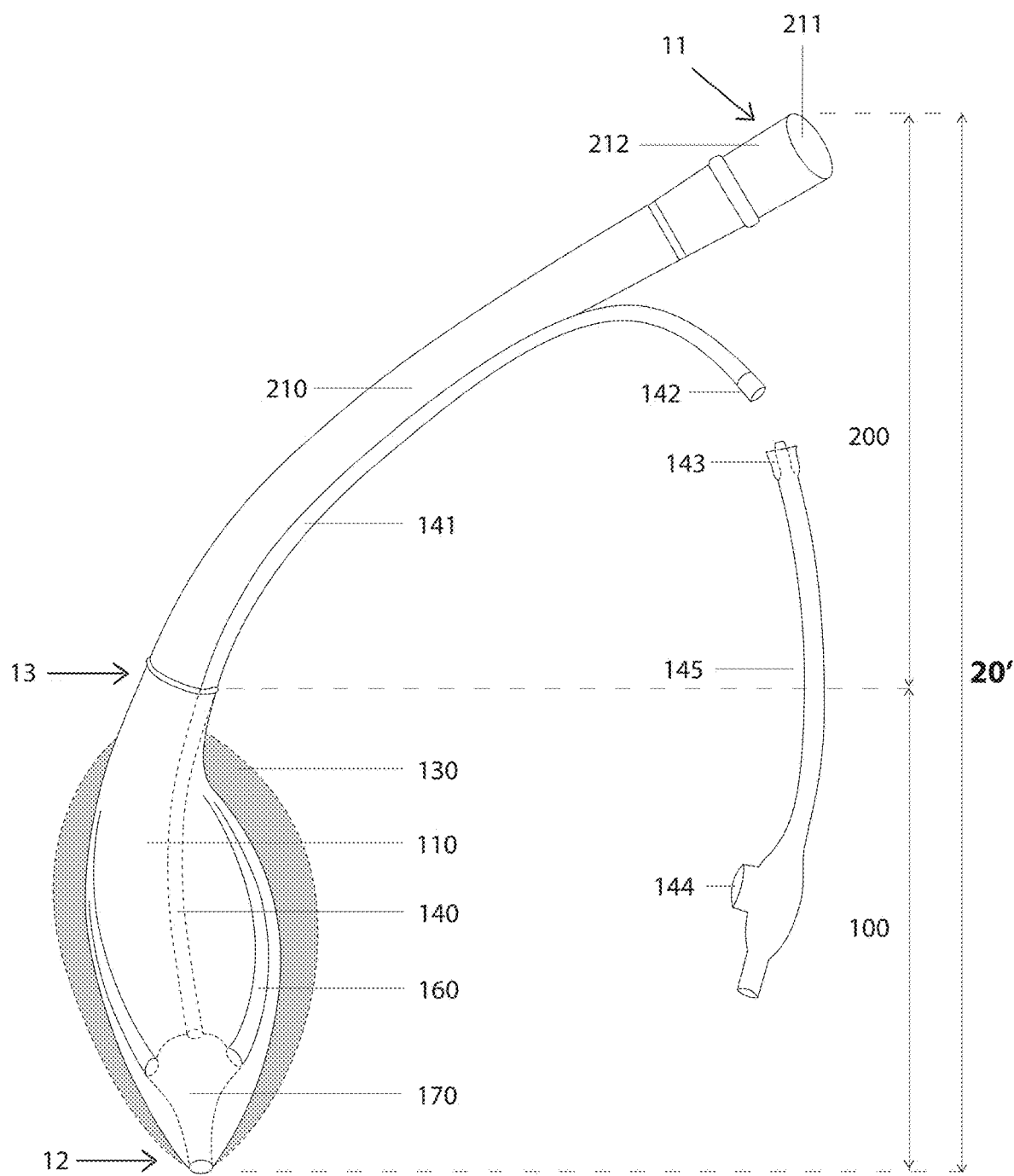

FIGS. 2A and 2B illustrate perspective views of an exemplary multi-channel flexible laryngeal mask airway devices 20 and 20', respectively, according to embodiments of the present disclosure. The airway devices 20 and 20' can be substantially similar in structure and function to the airway devices 10 and 10', except for the distinctions noted herein. Therefore, like reference numbers are used to refer to like structures. The airway devices 20 and 20' can include the mask portion 100 and the airway channel portion 200. The mask portion 100 can include the mask 110, the pharyngeal suction channel 140, the pharyngeal drains 160, and the ampulla 170. The ampulla 170, the pharyngeal drains 160 and a portion of a pharyngeal suction channel 140 can be formed on and/or embedded within the mask 110 or mask portion 100. As shown in FIGS. 2A and 2B, the airway devices 20 and 20' can be devoid of a gastric-pharyngeal access channel 150. As shown in FIG. 2A, the pharyngeal suction catheter 141 can be disposed within the interior volume of the airway channel 210 and can terminate and exit the airway channel 210 as the female luer lock connector 142 below an airway connector 212 near the proximal end 11 of the airway channel 210. As shown in FIG. 2B, the pharyngeal suction catheter 141 can be disposed outside of and along a length of the flexible airway channel 210 of the airway device 20'. The pharyngeal suction catheter 141 in airway device 20' can be attached to the outside of the airway channel 210 or can be free from the airway channel 210, and terminates as the free female luer lock connector 142. The female luer lock connector 142 of the airway devices 20 and 20' can be connected to a male luer lock connector 143 of an extension catheter 145 (FIG. 2A) as described herein. Like airway devices 10 and 10', the mask portion 100 of the airway devices 20 and 20' can cover and seal around the glottis and the flexible airway channel portion 200 of the airway devices 20 and 20' can extend from the mask portion 100 to the outside of the mouth when the airway device 20 or 20' is positioned in the upper airway of a human.

In an exemplary application, referring to FIGS. 2A and 2B, the airway device 20 or 20' can be inserted into the upper airway of a human such that the mask portion 100 is positioned in the hypopharynx of the human and the airway channel portion 200 extends from the mask portion such that the free terminal end of the airway channel 210 (i.e., the proximal end 11 of the airway device) and the port (luer lock connector) 142 of the pharyngeal suction channel 140 are positioned outside of a mouth of the human. When the airway device 20 or 20' is positioned in the upper airway of the human, the airway device 20 or 20' can allow access to the upper airway of the human for surgeries or procedures involving the upper airway. The airway device 20 or 20' can facilitate ventilation of lungs through the mask 110 and the flexible thin airway channel 210, while also providing evacuation of gastric and/or pharyngeal body fluid and/or blood during upper airway surgeries or procedures through a drainage and evacuation system formed by the pharyngeal suction channel 140, the pharyngeal drains 160, and the ampulla 170. Therefore, the airway device 20 or 20' can improve the safety of airway management and lung ventilation for upper airway surgeries, for example, by minimizing the risk of aspiration of blood or other fluid accumulated in the pharynx and possibly minimizing the risk of aspiration of gastric contents.

Figure 3:
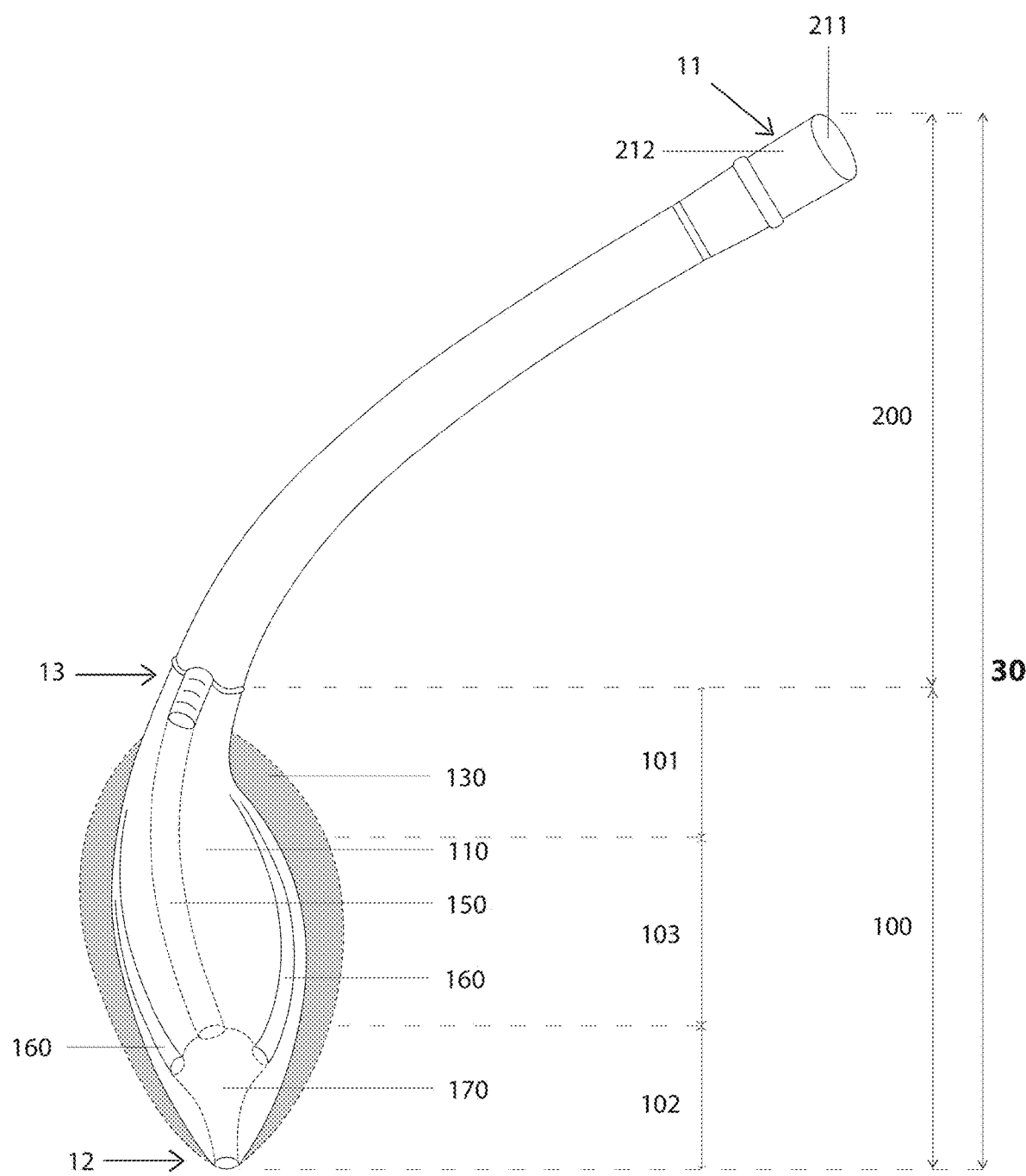
FIG. 3 illustrates a perspective view of an exemplary multi-channel flexible laryngeal mask airway device according to embodiments of the present disclosure, showing an evacuation system consisting of an ampulla-pharyngeal drains and a combined gastric-pharyngeal access channel integrated within the mask.

FIG. 3 illustrates a perspective view of an exemplary multi-channel flexible laryngeal mask airway device 30, according to embodiments of the present disclosure. The airway device 30 can be substantially similar in structure and function to the airway device 10, except for the distinctions noted herein. Therefore, like reference numbers are used to refer to like structures. The airway device 30 can include the mask portion 100 and the airway channel portion 200. The mask portion 100 can include the mask 110, the gastric-pharyngeal access channel 150, the pharyngeal drains 160, and the ampulla 170. As shown in FIG. 3, the airway device 30 can be devoid of the pharyngeal suction channel and the pharyngeal suction catheter. The gastric-pharyngeal access channel 150, the pharyngeal drains 160, and the ampulla 170 can be formed on and/or embedded within the mask 110 or mask portion 100. Like airway device 10, the mask portion 100 of the airway device 30 can covers and seals around the glottis and the flexible airway channel portion 200 can extend from the mask portion 100 to the outside of the mouth when the airway device 30 is positioned in the upper airway of a human.

In an exemplary application, referring to FIG. 3, the airway device 30 can be inserted into the upper airway of a human such that the mask portion 100 is positioned in the hypopharynx of the human and the airway channel portion 200 extends from the mask portion 100 such that the free terminal end of the airway channel 210 (i.e., the proximal end 11 of the airway device) is positioned outside of a mouth of the human. When the airway device 30 is positioned in the upper airway of the human, the airway device 30 can allow access to the upper airway of the human for surgeries or procedures involving the upper airway. When the airway device 30 is positioned in the upper airway of the human, the airway device 30 can facilitate ventilation of lungs through the mask 110 and the flexible thin airway channel 210, while also providing evacuation of gastric and/or pharyngeal body fluid and/or blood during upper airway surgeries or procedures through an evacuation system embedded in and integrated with the airway device, that is, through an evacuation system formed by the gastric-pharyngeal access channel 150, the pharyngeal drains 160, and the ampulla 170. Therefore, the airway device 30 can improve the safety of airway management and lung ventilation for upper airway surgeries, for example, by minimizing the risk of aspiration of blood or other fluid accumulated in the pharynx as well as minimizing the risk of aspiration of gastric contents.

Figure 4A:
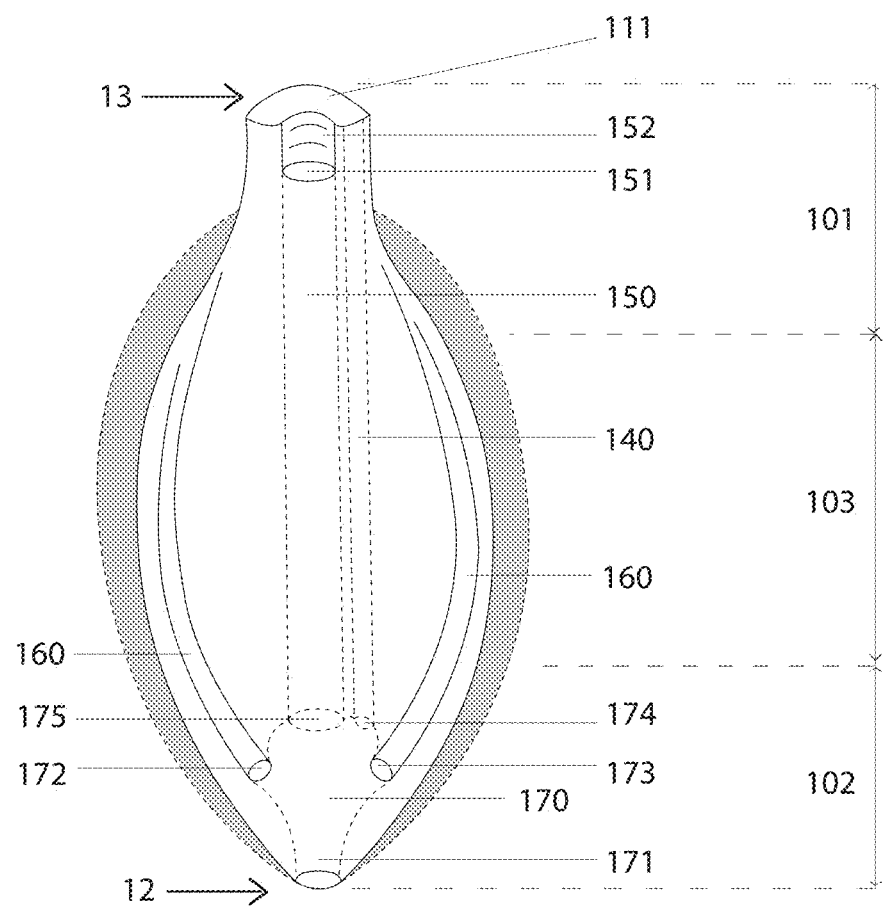
FIG. 4A illustrates a prospective posterior view of a mask portion of an embodiment of the airway devices of FIGS. 1A and 1B according to embodiments of the present disclosure showing the gastric-pharyngeal access channel and the pharyngeal suction channel embedded in the back of the mask and extending, in parallel with each other, from the ampulla toward the mask-airway channel junction, and the two pharyngeal drains on the back and along the edges of the mask emptying into the ampulla.
Figure 4B:
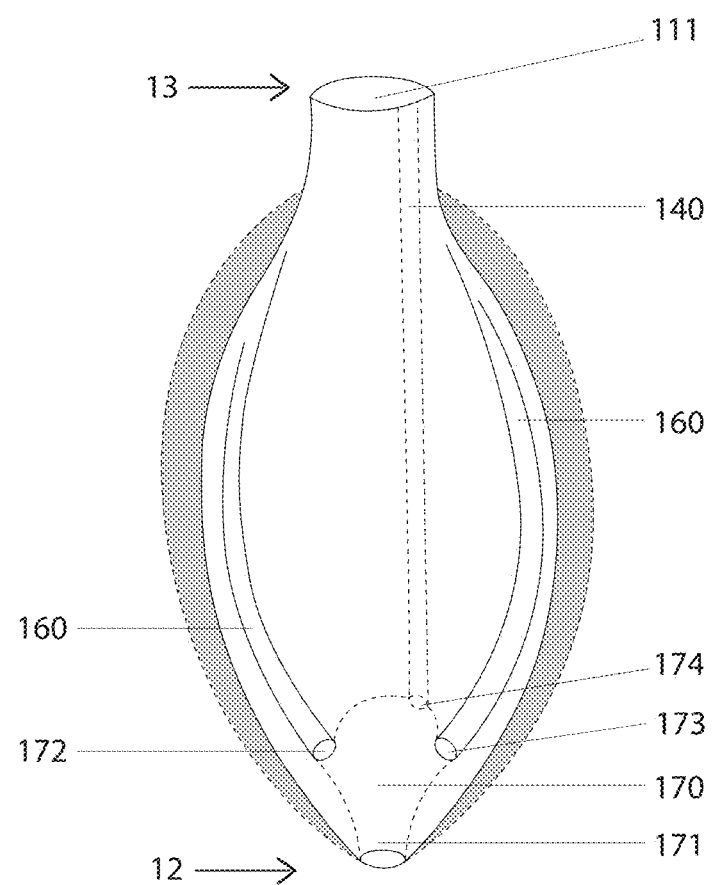
FIG. 4B illustrates a prospective posterior view of a mask portion of an embodiment of the airway devices of FIGS. 2A and 2B according to embodiments of the present disclosure.
Figure 4C:
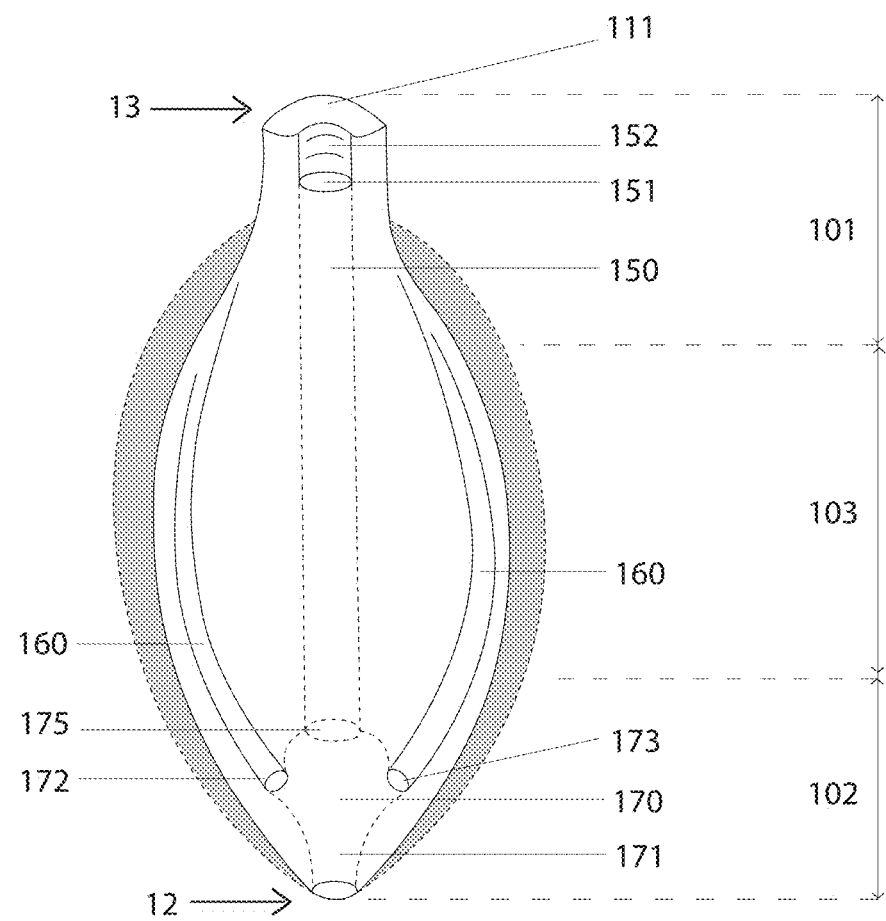
FIG. 4C illustrates a perspective posterior view of a mask portion of an embodiment of the airway device of FIG. 3 according to embodiments of the present disclosure.

FIGS. 4A and 5A-C illustrate the mask portion of the airway devices 10 and 10' of FIGS. 1A and 1B in more detail. FIG. 4B illustrates the mask portion of the airway devices 20 and 20' of FIGS. 2A and 2B in more detail. FIGS. 4C and 6A-C illustrates the mask portion of the airway devices 30 of FIG. 3 in more detail. As described herein, the mask portion of the airway device 20 and 20' is devoid of the gastric-pharyngeal access channel and the mask portion of the airway device 30 is devoid of the pharyngeal suction channel. The mask 110 can have a pear-shaped dome structure with an angulated and elongated opening 111 on the back side of the mask 110 at the first or proximal end (e.g., a top of the mask toward the base or upper part of the mask) where the airway channel 210 interfaces with the mask 110 at the junction 13 and is in fluid communication with an interior space 180 defined by the front side of the mask under the dome of the mask. The mask 110 may be made of materials such as PVC, silicone or styrene ethylene butadiene styrene that are firm enough to maintain the shape of the dome and the angle of the opening 111. The mask 110 can be surrounded by a soft edge such as the inflatable membrane cuff or other cushion materials 130, which can form or create a seal around the glottis of a human. The soft edge of the cuff or cushion 130 can be formed from one or more materials and by one or more methods of construction. If a membrane cuff is used, the cuff can be inflated either through tubing or automatically through the airway channel during positive pressure ventilation. With the soft edge of the cuff or cushion 130, the mask 110 covers and seals around the glottis when placed properly in the hypopharynx.

The apex 102 (e.g., proximate to the second end or lower part defined at the distal end 12) of the mask 110 encloses the ampulla 170, which includes ports 171-175. The ampulla can be an enclosed chamber or cavity accessible via the ports 171-175 which can form openings to the interior volume of the ampulla 170. The ampulla can have a generally bulbous or spherical internal volume. For embodiments of the mask portion that do not include the gastric-pharyngeal access channel 150, the ampulla 170 can be devoid of the port 175, as shown in FIG. 4B. For embodiments of the mask portion that do not include the pharyngeal suction channel 140, the ampulla 170 can be devoid of the port 174, as shown in FIGS. 4C and 6A-C. The port 175 forms an upper port of the ampulla 170 and connects the ampulla 170 to the gastric-pharyngeal access channel 150 such that the ampulla 170 and the gastric-pharyngeal access channel 150 can be in fluid communication with each other. The port 171 forms a distal or lower port of the ampulla 170 and opens to the upper esophagus when the mask portion 100 is positioned in the hypopharynx of a human. The ports 171 and 175 can be opposingly spaced and aligned with each other. The ports 172 and 173 of the ampulla 170 can be formed on opposing sides of the ampulla (i.e. one on each side of the ports 171 and 175). The ports 172 and 173 can be offset from the port 175 towards the distal end 12 of the mask portion 100 and can open towards the port 171. The port 174 of the ampulla 170 can be disposed adjacent to the port 175 between the port 175 and the port 172 (or port 173).

Figure 5A:
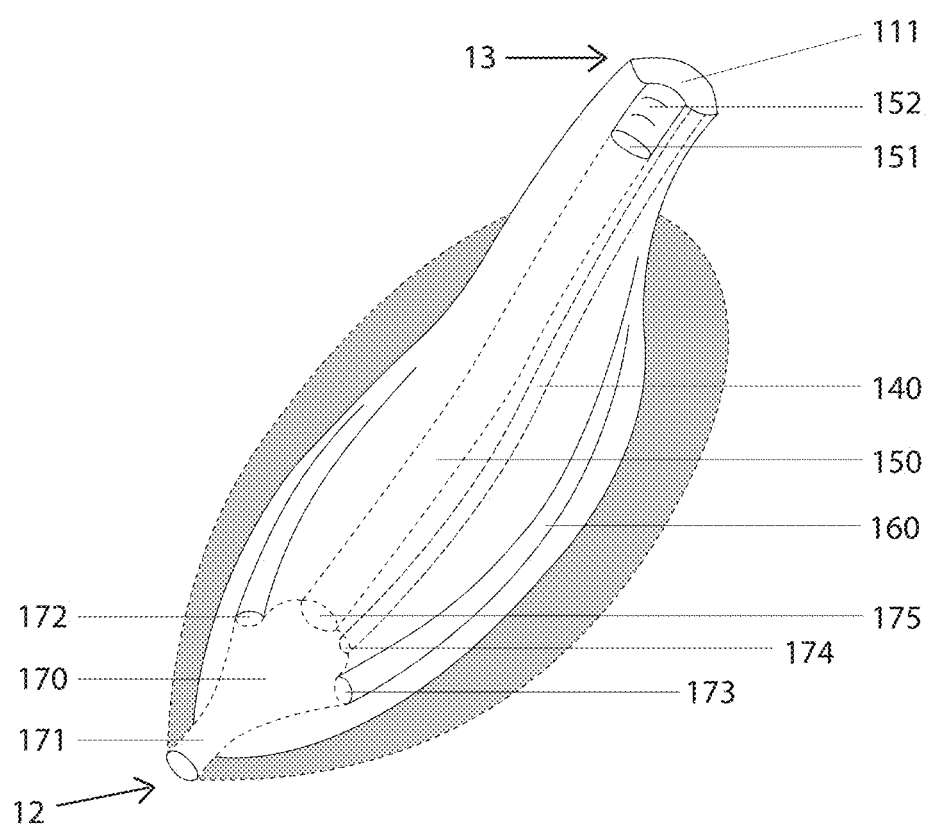
FIG. 5A illustrates a perspective posterior view of a mask portion of an embodiment of the multi-channel flexible laryngeal mask airway devices of FIGS. 1A and 1B showing the gastric-pharyngeal access channel and the pharyngeal suction channel embedded in the back of the mask and extending, in parallel with each other, from the ampulla toward the mask-airway channel junction, and the two pharyngeal drains on the back and along the edges of the mask emptying into the ampulla.
Figure 5B:
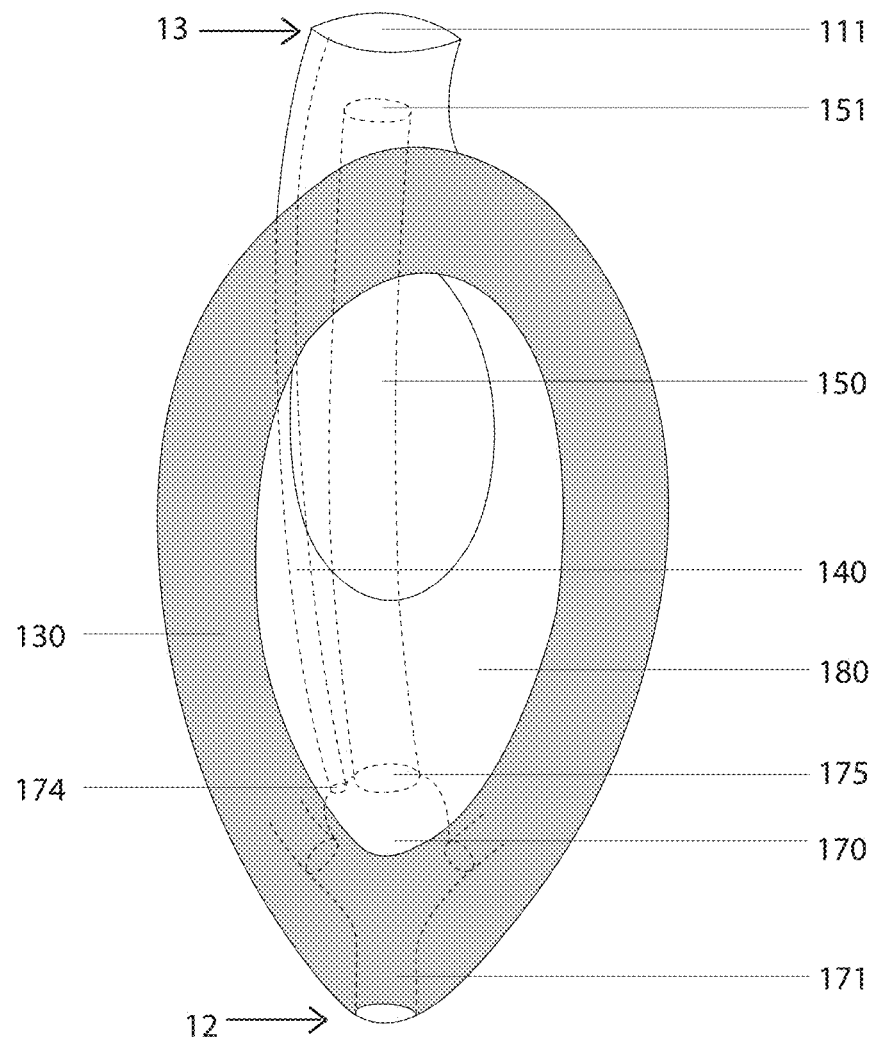
FIG. 5B illustrates a right anterior view of a mask portion of an embodiment of the airway devices of FIGS. 1A and 1B, showing the gastric-pharyngeal access channel and the pharyngeal suction channel traveling in parallel through, and embedded in, the mask, and merging with an ampulla at an apex of the mask portion.
Figure 5C:
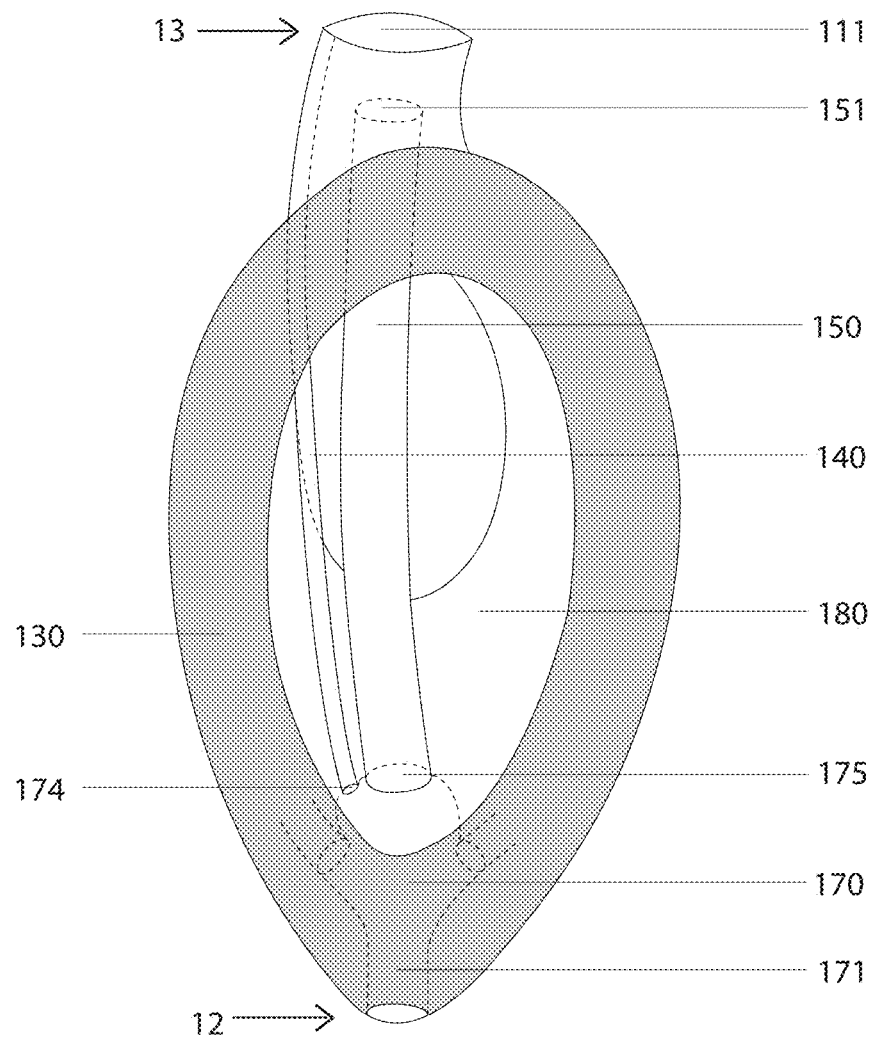
FIG. 5C illustrates a right anterior view of a mask portion of an embodiment of the airway devices of FIGS. 1A and 1B, showing the gastric-pharyngeal access channel and the pharyngeal suction channel entering and passing through the interior space under a dome of the mask before merging with an ampulla at an apex of the mask portion according to embodiments of the present disclosure.

The pharyngeal suction channel 140 can be formed on or integrated with the mask 110, and can extend from the upper port 174 of the ampulla to the base 101 of the mask. The pharyngeal suction channel 140 can be embedded within the back of the mask and travel along the spine of the mask (FIG. 5B) or can be formed and travel in the dome beneath the back of the mask (FIG. 5C). At the mask-airway channel junction 13, the pharyngeal suction channel 140 continues as a non-rigid catheter 141 inside or outside of the airway channel 210. The pharyngeal suction channel 140 is configured and dimensioned to allow for effective suction and evacuation of fluid or blood collected in the ampulla 170 via the pharyngeal drains 160.

Figure 6A:
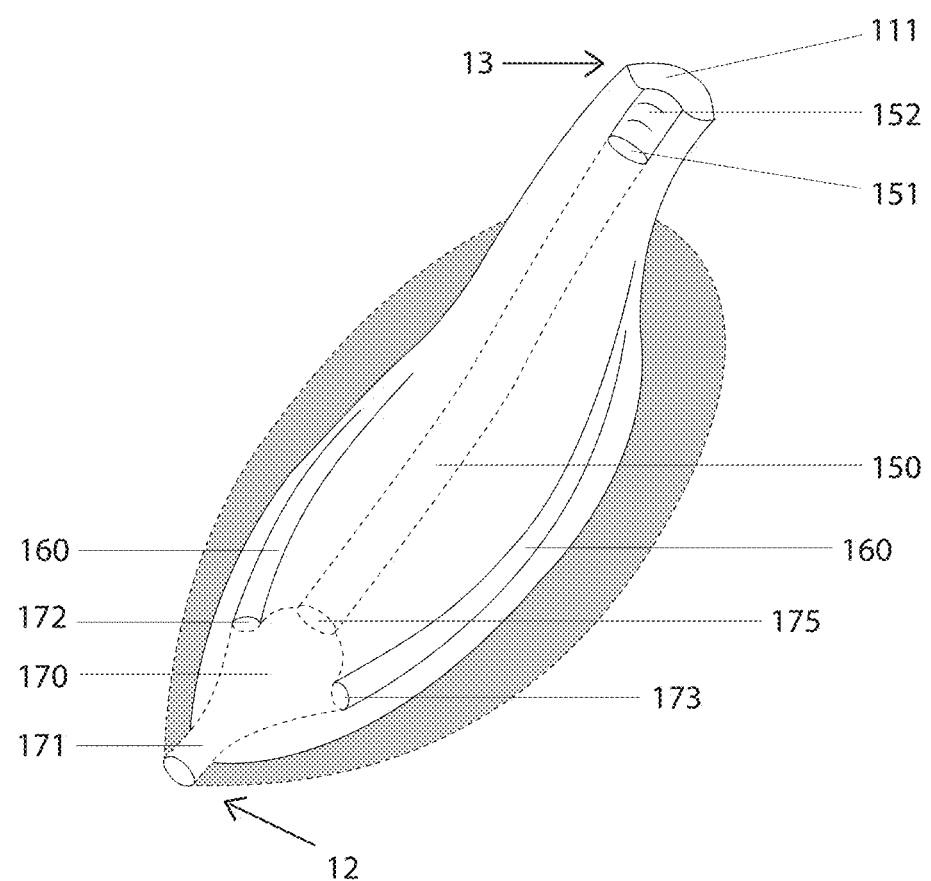
FIG. 6A illustrates a perspective posterior view of a mask portion of exemplary multi-channel flexible laryngeal mask airway device of FIG. 3 according to embodiments of the present disclosure showing the gastric-pharyngeal access channel embedded in the back of the mask and extending from the ampulla toward the mask-airway channel junction, and the two pharyngeal drains on the back and along the edges of the mask emptying into the ampulla.
Figure 6B:
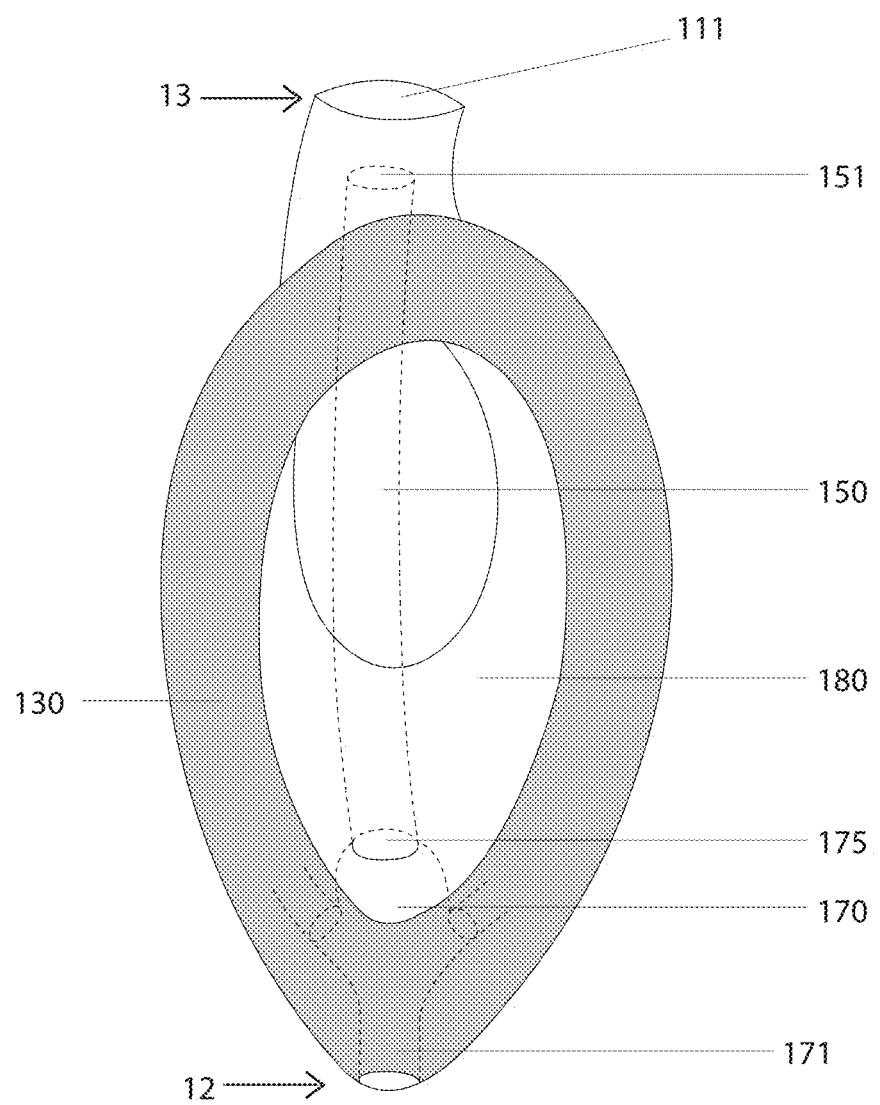
FIG. 6B illustrates a right anterior view of a mask portion of an embodiment of the airway device of FIG. 3, showing the interior space under a dome of the mask with the gastric-pharyngeal access channel embedded within the mask.
Figure 6C:
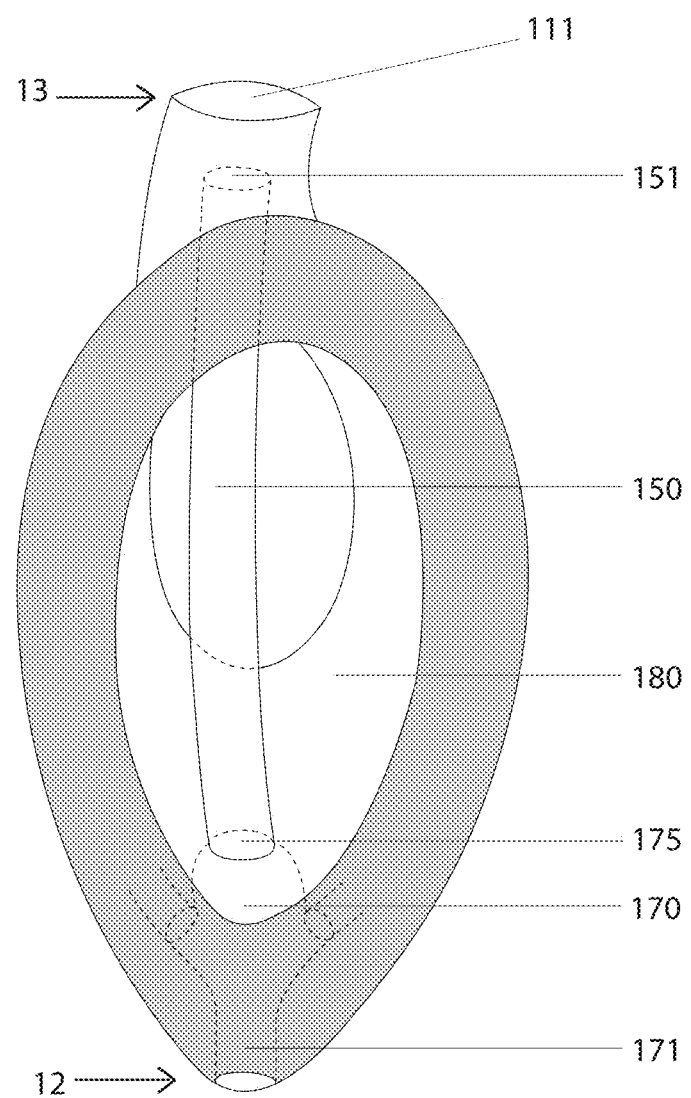
FIG. 6C illustrates a right anterior view of a mask portion of an embodiment of the airway device of FIG. 3, showing a gastric-pharyngeal access channel entering and passing through an interior space under a dome of the mask before merging with the ampulla at an apex of the mask portion according to embodiments of the present disclosure.

The gastric-pharyngeal access channel or gastropharyngeal channel 150 can be formed on or embedded in and integrated with the mask 110, and can extend from an opening 151 on the back of the mask, proximate to the first or proximal end (e.g. near the base 101) of the mask portion, to the upper port 175 of the ampulla 170 in the apex 102 of the mask 110. The gastric-pharyngeal access channel 150 can travel along the spine of the mask and enter the ampulla 170 at the upper port 175 to face the lower or distal port 171, which opens to the upper esophagus when the airway device is properly positioned in the hypopharynx of a human. In one embodiment, the gastric-pharyngeal access channel 150 itself (as shown in FIG. 6B) or along with the pharyngeal suction channel 140 (as shown in FIG. 5B) can be embedded in the mask 110, where the gastric-pharyngeal access channel 150 extends along the center line of the mask 110 to form part of a spine of the mask 110. In another embodiment, the gastric-pharyngeal access channel 150 itself (as shown in FIG. 6C) or along with the pharyngeal suction channel 140 (as shown in FIG. 5C) can penetrate the back of the mask 110 to the front side of the mask, entering and passing through the interior volume 180 under a dome of the mask 110 before merging with the ampulla 170 via the upper ports 174 and 175, respectively. In some embodiments, one of the pharyngeal suction channel 140 and the gastric-pharyngeal access channel 150 can be embedded in the mask 110, and the other one can pass through the interior volume 180 under the dome of mask 110 before merging with the ampulla 170.

The gastric-pharyngeal access channel 150 can be configured and dimensioned to receive a gastric suction tube or gastric-pharyngeal dual suction tube (DST) as described herein. For example, a cross-sectional area of the gastric-pharyngeal access channel 150 can be configured and dimensioned to allow for the passage of an appropriately sized gastric suction tube or gastric-pharyngeal dual suction tube DST (e.g. a size 12-18F for an adult). As an example, to accommodate a size 12-18F tube, the cross-sectional dimensions of the combined gastric-pharyngeal access channel 150 can be approximately five (5) millimeters by approximate eight (8) millimeters. In exemplary embodiments, the gastric-pharyngeal access channel can have generally oval cross-sectional shape.

A ramp 152 can be formed on the back of the mask from mask-airway channel junction 13 to the opening 151 of the gastric-pharyngeal access channel 150. The ramp 152 provides a guide for entry to the proximal opening 151 of the gastric-pharyngeal access channel 150. The ramp can be as a shallow recess formed in the back of the mask at the base 101 of the mask. The depth of the recess can gradually increase towards the opening 151 until the ramp 152 reaches the opening 151 at which point the depth of the recess of the ramp 152 can generally correspond to a depth of a bottom portion of the opening 151.

The pharyngeal drains 160 can be formed on or in the back of the mask 110. The pharyngeal drains 160 can extend along the side edges of the mask 110 from base 101 of the mask 110 towards the apex 102 of the mask 110. For example, the pharyngeal drains 160 can originate at the top of the mask 110, on the sidewalls of the mask 110 near the airway channel-mask junction 13 as small and shallow grooves or recesses. The pharyngeal drains 160 can gradually increase in width and depth before merging into the side ports 172 and 173 of the ampulla 170 near the apex 102 of the mask to form an ampulla-pharyngeal drain system. When the mask portion is positioned in the hypopharynx to cover and/or seal around the glottis, pharyngeal body fluid and/or blood can be collected by pharyngeal drains 160 during upper airway surgeries or procedures and can flow into the ampulla 170 where it can be removed through the pharyngeal suction channel 140 or using a suction tube via the gastric-pharyngeal access channel 150 as described herein. The high origination of the pharyngeal drains 160 provides air entry to the ampulla-pharyngeal drain system during suction, thereby preventing vacuum injury to the pharyngeal mucosa.

Figure 7A:
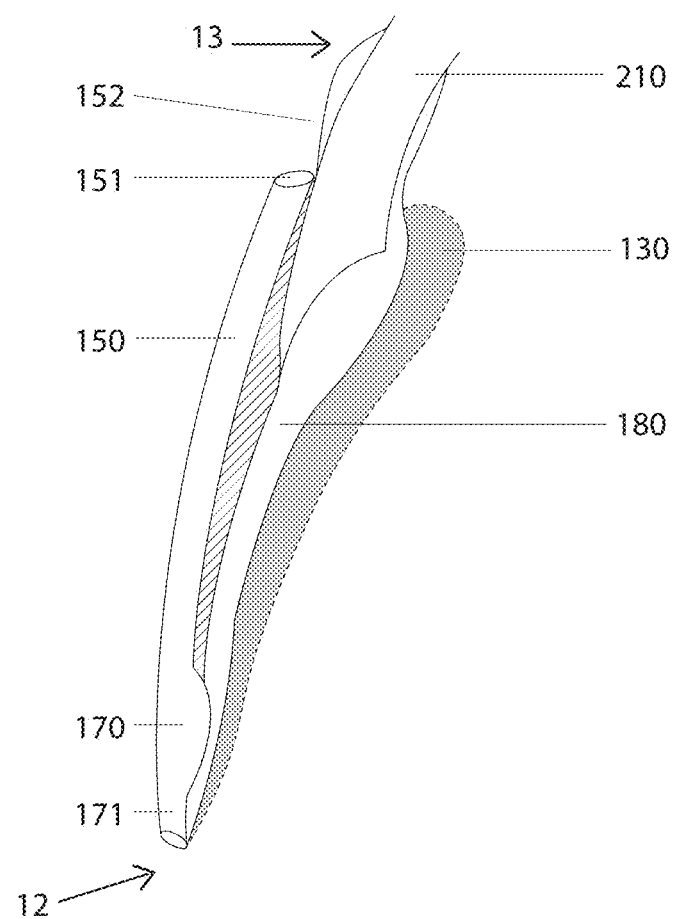
FIG. 7A illustrates sagittal view through a spine of a mask portion of an exemplary multi-channel flexible laryngeal mask airway device, showing a gastric-pharyngeal access channel, which originates at the base of the mask, travels along the spine of the mask, and enters an ampulla according to embodiments of the present disclosure.
Figure 7B:
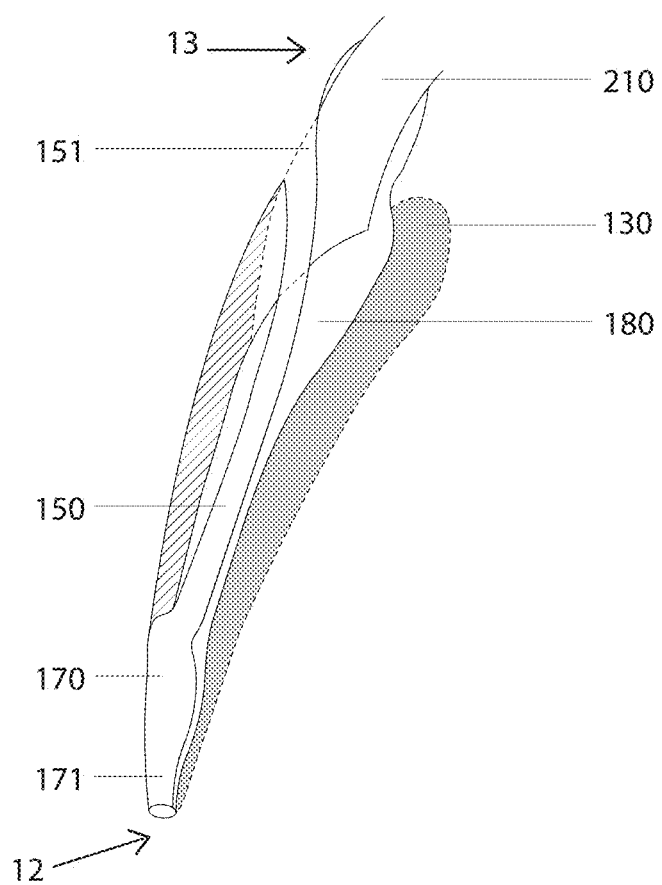
FIG. 7B illustrates a sagittal view of a mask portion of an exemplary airway device, showing a gastric-pharyngeal access channel entering a dome of the mask portion, passing through an interior space under the dome before merging with an ampulla at an apex of the mask portion according to embodiments of the present disclosure.

FIGS. 7A-B illustrate sagittal cross-sectional views, cut through the spine or centerline of the mask portion 100 in accordance with embodiments of the present disclosure. As shown in FIG. 7A, in one embodiment, the gastric-pharyngeal access channel 150, which originates proximate to the mask-airway channel junction 13, travels along the spine of the mask, and enters the ampulla 170 at port 175 facing the distal port 171 of the ampulla. The gastric-pharyngeal access channel 150 can be contained within the mask portion bounded by mask-airway channel junction 13 and the distal end 12 (i.e., the ends of the gastric-pharyngeal access channel can terminate within the mask portion). The opening 151 can open to the atmosphere or surrounding environment. The gastric-pharyngeal access channel 150 originates with the opening 151 at the first end or the base 101 of the mask. The ramp 152 slopes towards the opening 151 to provide a guide for inserting a tube, such as a suction tube, into the combined gastric-pharyngeal access channel 150. As shown in FIG. 7B, in another embodiment, the gastric-pharyngeal access channel 150 can enter the dome of the mask, passing through the interior volume 180 under the dome, and merge with the ampulla 170 at port 175. For embodiments that include both the gastric-pharyngeal access channel 150 and the pharyngeal suction channel 140 (e.g., the airway devices 10 and 10' shown in FIGS. 1A-B), the pharyngeal suction channel 140 can travel generally parallel to and along with the gastric-pharyngeal access channel in the mask portion 100 and can be embedded in the mask or attached underneath the mask, as described herein.

Figure 7C:
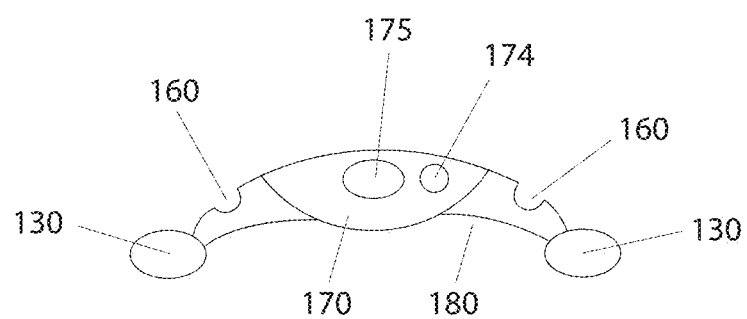
FIG. 7C illustrates a coronal view, through a top boundary of an ampulla of a mask portion of an exemplary multi-channel flexible laryngeal mask airway device, showing upper ports of the ampulla, with the relation to pharyngeal drains on a back of the mask according to embodiments of the present disclosure.

FIG. 7C illustrates a coronal cross-section view of the mask portion cut through the upper edge of the ampulla 170 of the airway device 10 or 10' shown in FIGS. 1A and 1B. The coronal cross-section view shows the upper port 175 to the gastric-pharyngeal access channel 150 and the upper port 174 to the pharyngeal suction channel 140 in relation to the pharyngeal drains 160 on the back of the mask. The port 175 can be larger in diameter than the port 174, and the port 174 can be offset to one side of the mask 110. The port 175 can be generally aligned with a center line of the mask 110. For embodiments that do not include the pharyngeal suction channel 140 (e.g., the airway device 30 shown in FIG. 3), the ampulla 170 does not include the port 174 and for embodiments that do not include the gastric-pharyngeal access channel (e.g., airway devices 20 and 20' shown in FIGS. 2A and 2B), the ampulla 170 does not include the port 175. As shown in FIG. 7C, the pharyngeal drains 160 can be formed as recesses in the back of the mask 110 near, but inward of, the edge or perimeter of the mask 110.

FIG. 10 shows a detailed view of the ampulla of embodiments of the present disclosure and a configuration of the port 171. In exemplary embodiments, as shown in FIG. 10, the distal port 171 can be approximately five millimeters to approximately eighteen millimeters or approximately eight millimeters to approximately fifteen millimeters in length (L). The distal port 171 can have a funnel-like shape such that the distal port 171 tapers inwardly as it extends from the ampulla 171 to the distal end 12 of the airway device such that a cross-sectional area of the distal port gradually decreases as the distal port extends towards the distal end 12 from the ampulla 170. As an example, as shown in FIG. 10, a cross-section of an end of the distal port proximate to the ampulla (e.g., an upper end of the distal port 171) can have dimensions (W1) of approximately five (5) millimeters by approximately six (6) millimeters and a cross-section of an end of the distal port proximate to the distal end 12 of the airway device (e.g., a lower end of the distal port) can have dimensions (W2) of approximately four and five tenths (4.5) millimeters by approximately four and five tenths (4.5) millimeters.

In some embodiments, the ampulla 170 can include a distal valve 176 covering the distal opening of the port 171 (FIG. 10 insertion). In some embodiments, the ampulla is devoid of the valve 176. In it closed or normal state, the distal valve can be a tri-leaflet membrane that has a center hole 178, which can be approximately one millimeter (1 mm) in diameter, and each leaflet 177 of the tri-leaflet configuration can engage and/or overlap adjacent leaflets. In the closed or normal state, the leaflets 177 can extend radially inwardly towards the center hole. The leaflets 177 can be hinged along a perimeter of the distal end of the port 171 to facilitate rotation or deformation of the leaflets 177 outwardly away from the distal end of the port (e.g., upon introduction of a DST) to an open state and to facilitate rotation of the leaflets 177 inwardly towards the distal end of the port 171 back to the closed state absent any structure or force holding the valve in the open state. In its closed state, the tri-leaflet distal valve 176 can function to block or retard fluid drainage from the ampulla 170 into the esophagus, e.g., when there is no DST inserted through the distal port 171, while allowing air vent out of the esophagus or stomach, which prevents air insufflation of the stomach due to air leaking from the airway through the laryngeal mask airway device during positive pressure ventilation. As an example, in the closed state, the tri-leaflets valve 176 can sustain a pressure of 5 cmH2O from the fluid accumulated in the ampulla 170 but can allow for venting of air or fluid with pressure high than 5 cmH2O from the esophagus or stomach or with vacuum applied to the ampulla. The tri-leaflets valve 176 allows for passage of an appropriately-sized gastric suction tube to access the esophagus and/or stomach. The two side ports 172 and 173 of the ampulla 170 can be connected to and in fluid communication with the pharyngeal drains 160 on or in the mask.

FIGS. 8A-B and 9A-C illustrate perspective views of an exemplary gastric-pharyngeal dual suction tube (DST) 400 and 500, respectively, in accordance with embodiments of the present disclosure. The DSTs 400 and 500 can be formed of PVC or similar materials with suitable firmness for insertion into and through the gastric-pharyngeal access channel 150 of embodiments of the airway device 10, 10' or 30.

Figures 8A, 8B:
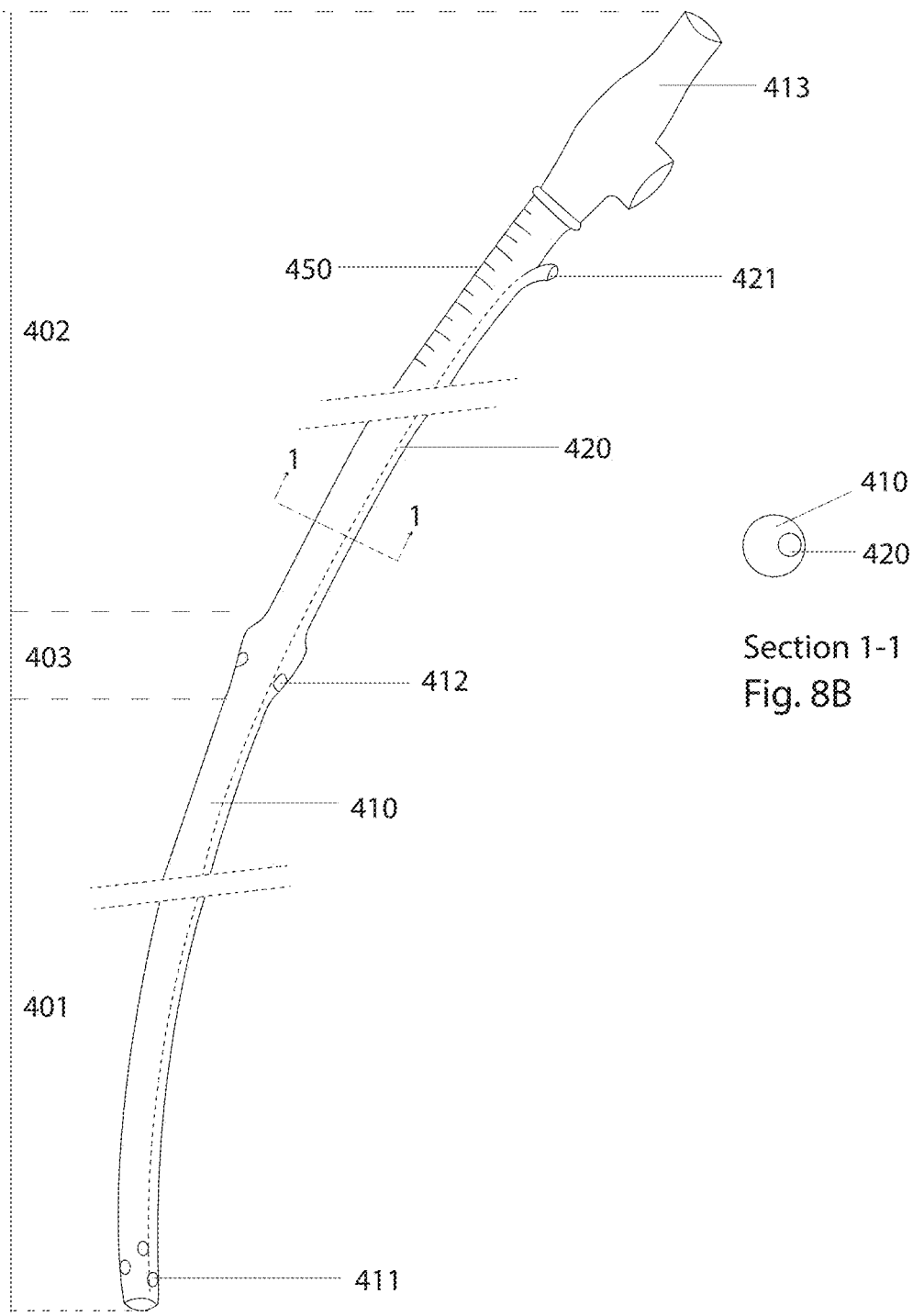
FIG. 8A illustrates a perspective view of an exemplary gastric-pharyngeal dual suction tube DST according to embodiments of the present disclosure.
FIG. 8B illustrates a cross-sectional view of the exemplary DST tube through line 1-1 in FIG. 8A according to embodiments of the present disclosure.

As shown in FIG. 8A, the DST 400 includes a lower or gastric section 401, an upper or pharyngeal section 402, and a transitional zone 403 connecting the lower and upper sections 401 and 402. The lower section 401 can include gastric eyelets or openings 411 and the transitional zone 403 can include pharyngeal eyelets or openings 412. The transitional zone 403 can serve as a distal portion of the upper section 402.

The DST 400 can include two lumens: the main or suction lumen 410 and the air lumen 420. The main lumen 410 is larger than the air lumen 420 and is the working lumen for suction and evacuation of bodily fluids. The proximal end of the main lumen 410 terminates as a three-way port 413, which allows for vacuum suction only through hand regulation and avoids continuous suction which may cause injury to the gastric mucosa. The air lumen 420 provides an air vent, which allows for atmospheric air to enter the tube through a proximal port 421 and equalize the vacuum pressure once the contents are removed, preventing vacuum injury to the mucosa.

The lower (gastric) section 401 can be configured and dimensioned to fit and pass through the gastric-pharyngeal access channel 150 as well as the funnel-shaped distal port 171 of the ampulla 170 of the airway devices 10, 10', and 30. For embodiments in which the distal port 171 includes the tri-leaflet valve 176, the lower section 401 can be configured and dimensioned to fit and pass through the tri-leaflet valve 176 to urge the tri-leaflet valve 176 to transition from its closed position to its open position. In exemplary embodiments, the lower section 401 can be approximately thirty-eight (38) centimeters to approximately forty-two (42) centimeters in length or approximately forty (40) centimeters in length. When the lower section 401 is positioned properly in the airway device 10 or 10' or 30 that is placed in the hypopharynx of a human, approximately fifteen (15) centimeters of the lower section 401 can be left in the stomach of an adult human.

Figure 15:
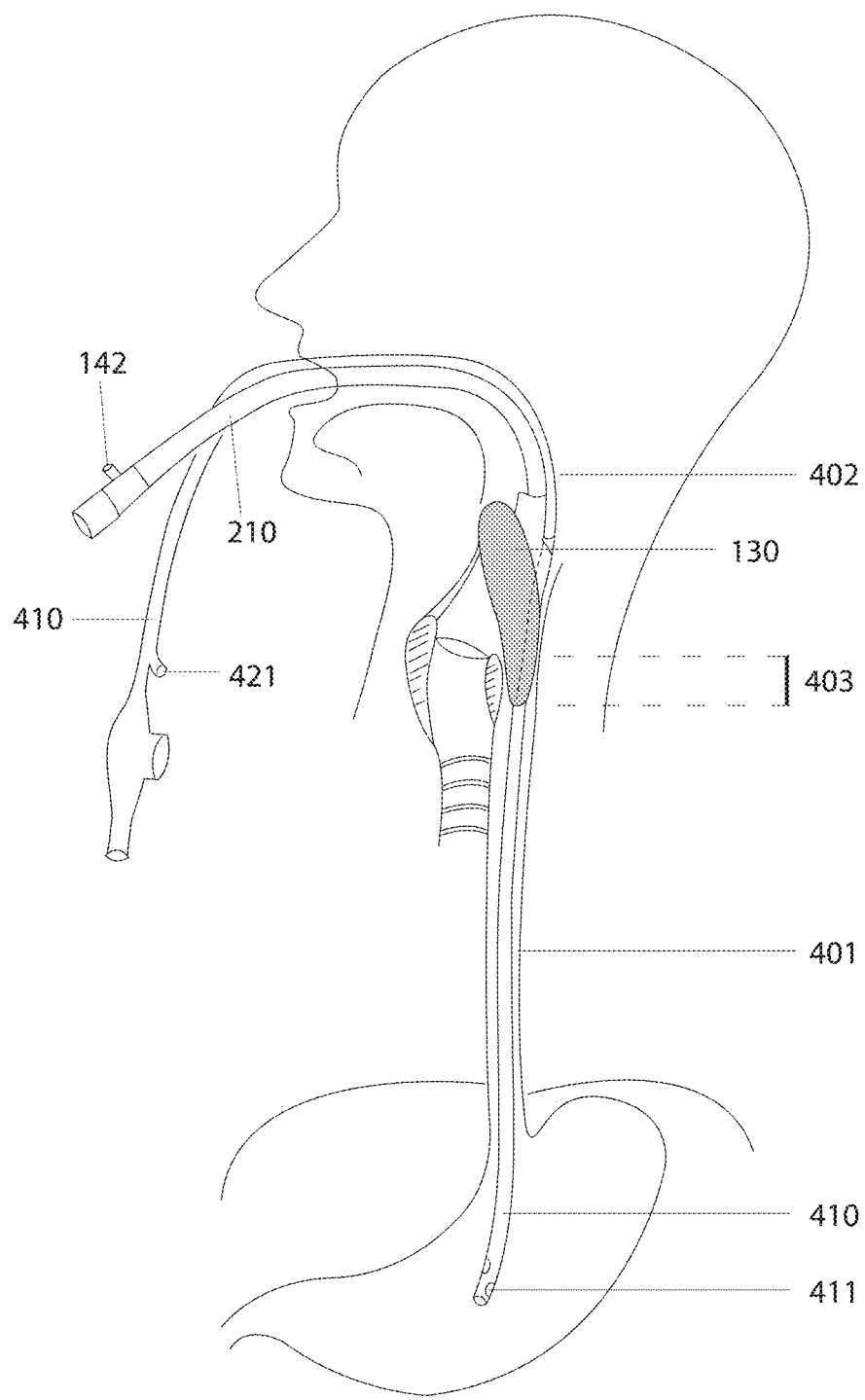
FIG. 15 illustrates a perspective view of an exemplary multi-channel flexible laryngeal mask airway device placed in the hypopharynx of a human, and an exemplary dual suction tube placed through a gastric-pharyngeal access channel of the airway device and into the human's esophagus and stomach with a distal part and gastric eyelets in the stomach while a proximal end extends outside the mouth according to embodiments of the present disclosure.

The upper (pharyngeal) section 402 and the transitional zone 403 can be configured and dimensioned to fit and pass through the gastric-pharyngeal access channel 150. However, as shown in FIG. 11A and referring to FIGS. 10 and 12A, the transitional zone 403 is configured and dimensioned to be too large to pass through the distal port 171 of the ampulla 170. As a result, the distal port 171 forms a stop structure such that the DST 400 is fully inserted when the transitional zone 403 abuts the distal port 171 of the ampulla. The upper section and the transitional zone combined are approximately thirty-three (33) centimeters to approximately thirty-eight (38) centimeters or approximately thirty-five (35) centimeters in length, such that when the transition zone 403 abuts the distal port 171 positioned in the upper airway of a human, approximately fifteen (15) centimeters of the DST 400 is outside the mouth in an adult (FIG. 15).

Referring to FIGS. 8A and 11A, the transitional zone 403 can have a generally truncated cone-shaped structure. The lower section 401 and the upper section 402 can have a first generally uniform cross-sectional area ($A_1$) along their lengths, although the lower section 401 can taper slightly at the distal end (FIG. 8A). At a transition between the upper section 402 and the transitional zone 403, the cross-sectional area of the DST 400 increases to a second cross-sectional area ($A_2$), which is greater than the first cross-sectional area, and then the cross-sectional area gradually decreases to return to the first cross-sectional area ($A_1$) at the transition from the transitional zone 403 to the lower section 401 (FIG. 11A). The transitional zone 403 can have a length ($L_T$) of approximately eight (8) millimeters to approximately twelve (12) millimeters or approximately ten (10) millimeters. The distal end of the transitional zone 403 (i.e., the transition from the transitional zone 403 to the lower section 401) can have dimensions ($W_{T1}$) of approximately four millimeters by approximately four millimeters (4×4 mm), which fits through the gastric-pharyngeal access channel 150 having a dimension (W) of up to approximately five by approximately eight millimeters (5×8 mm), and can enter the distal port 171 of the ampulla 170, which has dimensions of approximately five by approximately six millimeters (5×6 mm) at the top (W1) and approximately four and five tenths by approximately four and five tenths (4.5×4.5 mm) at the bottom (W2), respectively (FIG. 10). However, the proximal or top end of the transitional zone 403 (i.e., the transition from the upper section 402 to the transitional zone 403) can have dimensions ($W_{T2}$) of approximately four millimeters by six and six tenths millimeters (4×6.6 mm), and thus cannot pass through the funnel-shaped distal port 171 of the ampulla, which has dimensions (W1) of five by six millimeters (5×6 mm) at the top (FIG. 10). Therefore, the transitional zone 403 serves as a functional separation of the gastric suction and the pharyngeal suction, and as a guide to the depth of insertion of the DST 400 into embodiments of the airway device 10, or 30 or 30', and into the stomach.

As described herein, the DST 400 can have two sets of suction eyelets: the gastric eyelets 411 and the pharyngeal eyelets 412. The first set or gastric eyelets 411 are located at the distal end of the tube, approximately 40 cm from the transitional zone 403, and are used for evacuating fluids from the stomach. The second set or pharyngeal eyelets 412 are located in the truncated cone-shaped transitional zone 403, about 35 cm from the proximal end, and are used for evacuating fluids from the pharynx through the ampulla-pharyngeal drains. As shown in FIGS. 8A and 11A, the pharyngeal eyelets 412 can be disposed proximate to the distal end of the transitional zone 403 (i.e., proximate to the transition from the transitional zone 403 to the lower section 401).

Figure 12B:
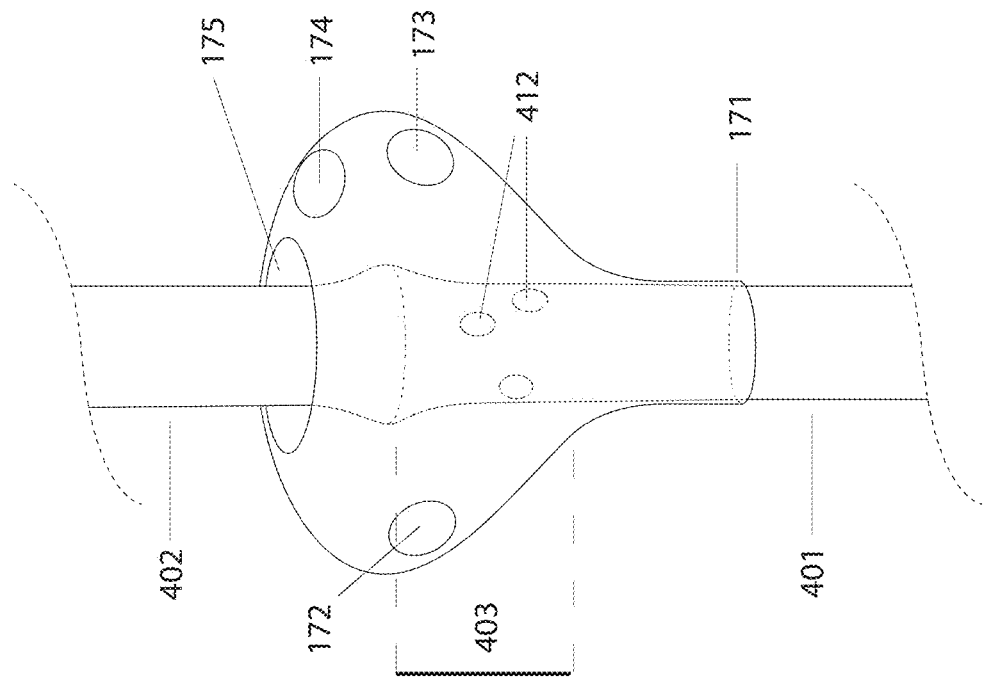
FIGS. 12A and 12B illustrate exemplarily a transitional zone of an embodiment of the DST of FIGS. 8A-B positioned in an ampulla in accordance with embodiments of the present disclosure.
Figure 12A:
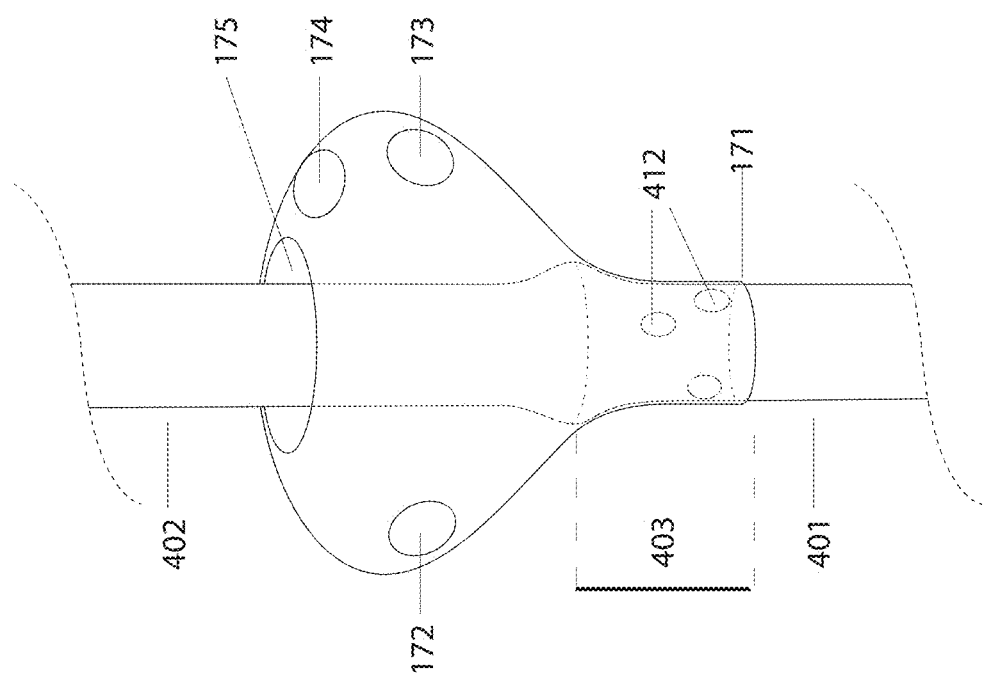

With reference to FIGS. 1A-B, 3, 8A, and 12A-B, the DST 400 can be used with an airway device that has a gastric-pharyngeal access channel 150 with or without a pharyngeal suction channel 140 (e.g., airway devices 10, 10', or 30 shown in FIGS. 1A, 1B, and 3). The DST 400 can be placed through the gastric-pharyngeal access channel via the proximal opening 151 located near the mask-airway channel junction 13. The lower section 401 can pass through the oval-shaped gastric-pharyngeal access channel 150 and the funnel-shaped distal port 171 of the ampulla 170, entering the esophagus and the stomach, until the cone-shaped transitional zone 403 reaches the funnel-shaped distal port 171 of the ampulla 170 where the DST 400 is prevented from being inserted further (FIGS. 12A and 14B). That is, the DST 400 can be configured and/or dimensioned to be inserted into the mask portion via the gastric-pharyngeal channel until the transitional zone engages the distal port 171 of the ampulla, which is configured and dimensioned to engage and stop the advancement of the dual suction tube 400. At this position, the gastric eyelets 411 are positioned in the stomach approximately 15 cm below the gastro-esophageal junction, while the pharyngeal eyelets 412 are blocked in the funnel-shaped distal port 171 of the ampulla and are not functional (FIGS. 12A and 14B). If access to the ampulla-pharyngeal drain system through the DST is needed, the DST 400 can be withdrawn about 5 to 8 mm to position the pharyngeal eyelets 412 in the ampulla 170 so they are no longer blocked by the distal port 171 (FIG. 12B). Mark lines 450 on the upper part of the dual suction tube 400 (FIG. 8A) can guide the withdrawal.

While FIG. 8A shows two sets of eyelets, embodiments of the DST 400 may include more or less sets of eyelets. For example, in one embodiment, the DST 400 can be devoid of the pharyngeal eyelets 412 so that the suction tube is a gastric suction tube without pharyngeal suction capability, while the transitional zone can still guide the depth of insertion.

FIG. 8B is a cross-sectional view of the DST 400 shown in FIG. 8A. As shown in FIG. 8B, the DST 400 can have a generally circular cross-sectional shape in the lower and upper sections 401 and 402. The air lumen 420 can be disposed within the DST 400.

Figure 9A:
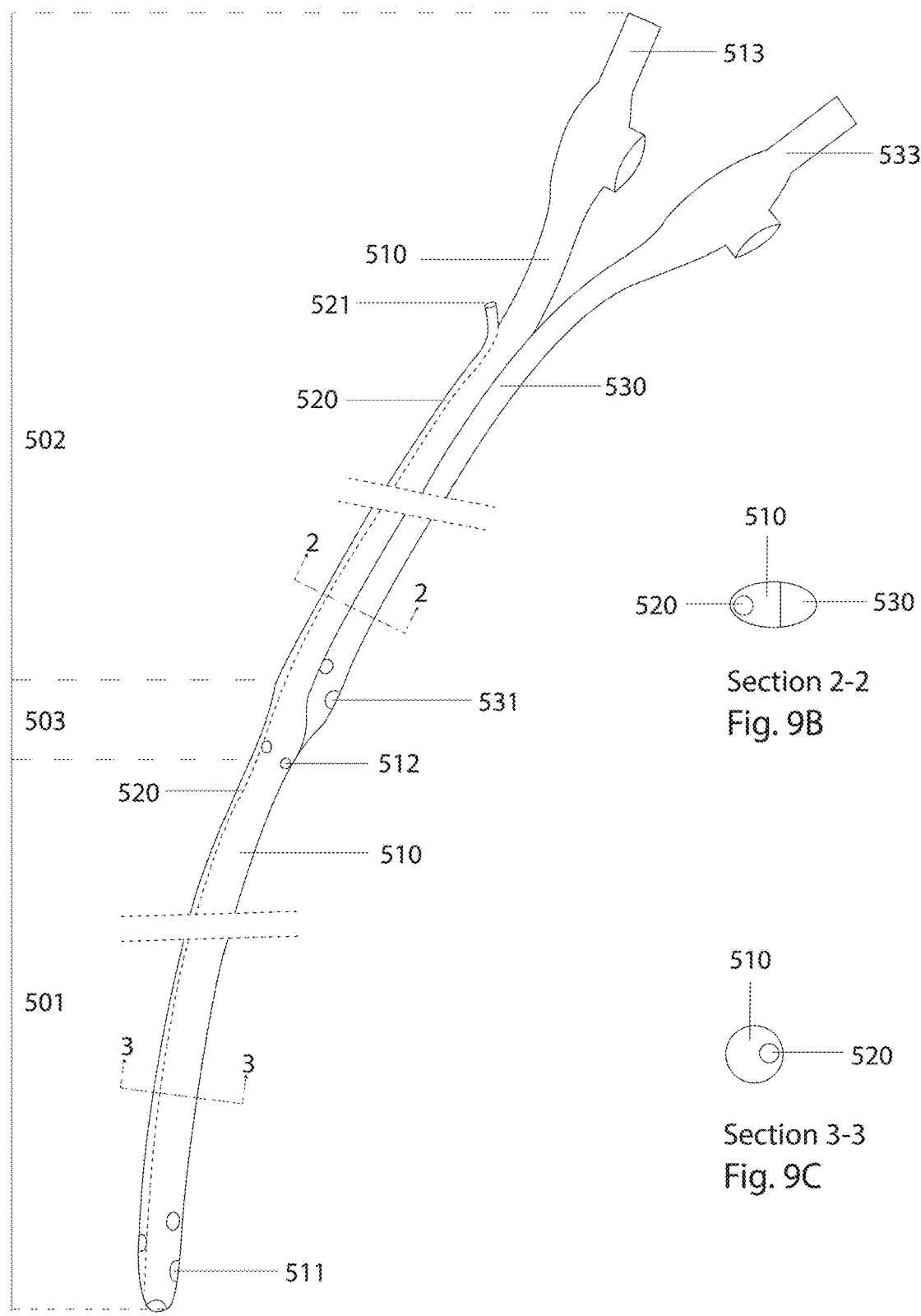
FIG. 9A illustrates a perspective view of another exemplary gastric-pharyngeal dual suction tube DST according to embodiments of the present disclosure.

As shown in FIG. 9A-C, the DST 500 includes three sections: a lower gastric section 501, an upper pharyngeal section 502, and a transitional section 503, which connects the lower and upper sections 501 and 502. The DST 500 can include three lumens: a gastric lumen 510, an air lumen 520, and a pharyngeal lumen 530.

The gastric lumen 510 can be the first and largest lumen, and is the working lumen for suction and evacuation of fluids from the stomach. The air lumen 520 can be the second and smallest lumen. Similar to air lumen 420 in DST 400, the air lumen 520 is for air vent—it travels along the gastric lumen and allows for atmospheric air to enter the stomach through a proximal port 521 and equalize the vacuum pressure once the gastric contents are removed, preventing vacuum injury to the mucosa. The pharyngeal lumen 530 can be the third lumen, and is the working lumen for suction and evacuation of fluids from the ampulla-pharyngeal drains. The pharyngeal lumen 530 has a length that extends from the proximal end of DST 500 to about the transitional zone 503. The pharyngeal lumen 530 can be terminated before reaching the transitional zone 503 (FIGS. 9A and 13A, 13B. The proximal ends of the two large lumens 510 and 530 each terminate as a three-way port 513 and 533, respectively, which can allow for vacuum suction only through hand regulation and avoids continuous suction that may cause injury to the mucosa.

The lower (gastric) section 501 can have a circular cross-section that is configured and dimensioned to fit and pass through the gastric-pharyngeal access channel 150 as well as the funnel-shaped distal port 171 of the ampulla. As an example, the lower section 501 can have diameter of approximately four (4) millimeters (FIG. 9C), and a length of approximately thirty-eight (38) centimeters to approximately forty-two (42) centimeters or can be approximately 40 cm in length. The lower section 501 can be dimensioned and configured to pass through the esophagus, leaving approximately 15 cm in the stomach in an adult, when the DST 500 is fully received in the airway device 10, or 10' or 30 positioned in the upper airway of a human.

Referring to FIGS. 9A-C, the upper (pharyngeal) section 502 and transition zone 503 can be configured and dimensioned to fit and pass through the gastric-pharyngeal access channel, but to be too large to pass through the funnel-shaped distal port 171 of the ampulla. The upper section 502 can have a length of approximately thirty-three (33) centimeters to approximately thirty-eight (38) centimeters or can be approximately thirty-five (35) centimeters in length, which, when positioned properly, leaves approximately fifteen (15) cm outside of the mouth in an adult.

As shown in FIGS. 9A and 11B, the lower section 501 can have a first generally uniform cross-sectional area ($A_1$) along its length, although the lower section 501 can taper slightly at the distal end. The upper section 502 can have a second generally uniform cross-sectional area ($A_2$) along its length. At a transition between the upper section 502 and the transitional zone 503, the cross-sectional area can be approximately the same of the second cross-sectional area ($A_2$), which is greater than the first cross-sectional area, and then the cross-sectional area of the transitional zone 503 gradually decreases to the first cross-sectional area ($A_1$) at the transition from the transitional zone 503 to the lower section 501 (FIG. 11B). As a result, the transitional zone 503 can have a generally truncated cone-shaped structure. Similar to the transitional zone 403 in the DST 400 and as shown in FIG. 11, the transitional zone 503 can have a dimension and configuration that can enter but cannot pass through the distal port 171 of the ampulla, that is, the diameter ($W_{T2}$) of the upper section 502 or the top of the transitional zone 503 is too large to fit the upper diameter ($W_1$) of the distal port 171. The transitional zone 503 of DST 500 provides a structural separation of the gastric suction and the pharyngeal suction such that two separated lumens can function simultaneously. In addition, the transitional zone ensures correct placement and position of the DST 500.

Referring to FIGS. 9A and 11B, the DST 500 has three sets of suction eyelets. The first set is the distal or gastric eyelets 511 of the gastric lumen, which are located at the distal end of the DST 500, approximately 40 cm from the transitional zone 503, and are used for evacuating fluids from the stomach. The second set is the proximal or pharyngeal eyelets 512 of the gastric lumen. The pharyngeal eyelets 512 are located in the truncated cone-shaped transitional zone 503 proximate to the transition between the transitional zone 503 and the lower section 501. The third set, absent in DST400, is the pharyngeal eyelets 531 of the pharyngeal lumen 530, which are located immediately above the truncated cone-shaped transitional zone 503, about 35 cm from the proximal end, and are used for evacuating the pharynx through the ampulla-pharyngeal drains. In some embodiments, the second set of eyelets 512 can be omitted as the second set of eyelets can operate only as a back-up system for the third set of eyelets 531, for evacuating the pharynx through the ampulla-pharyngeal drains.

Figure 13B:
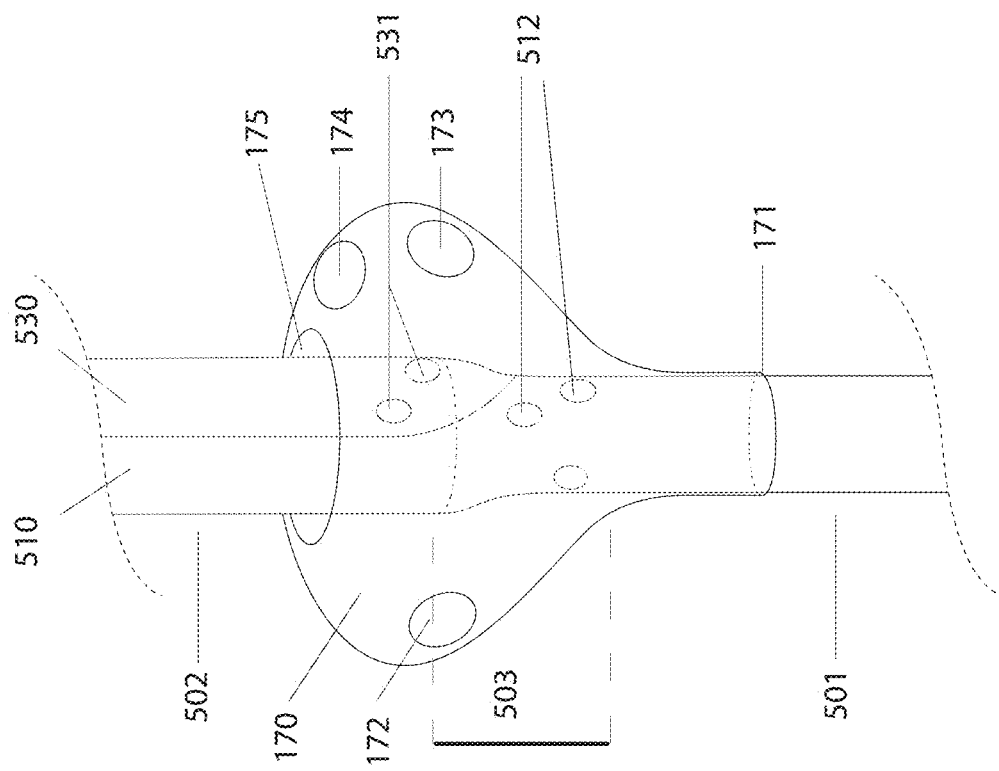
FIGS. 13A and 13B illustrate exemplarily a transitional zone of an embodiment of the DST of FIGS. 9A-C positioned in an ampulla in accordance with embodiments of the present disclosure.
Figure 13A:
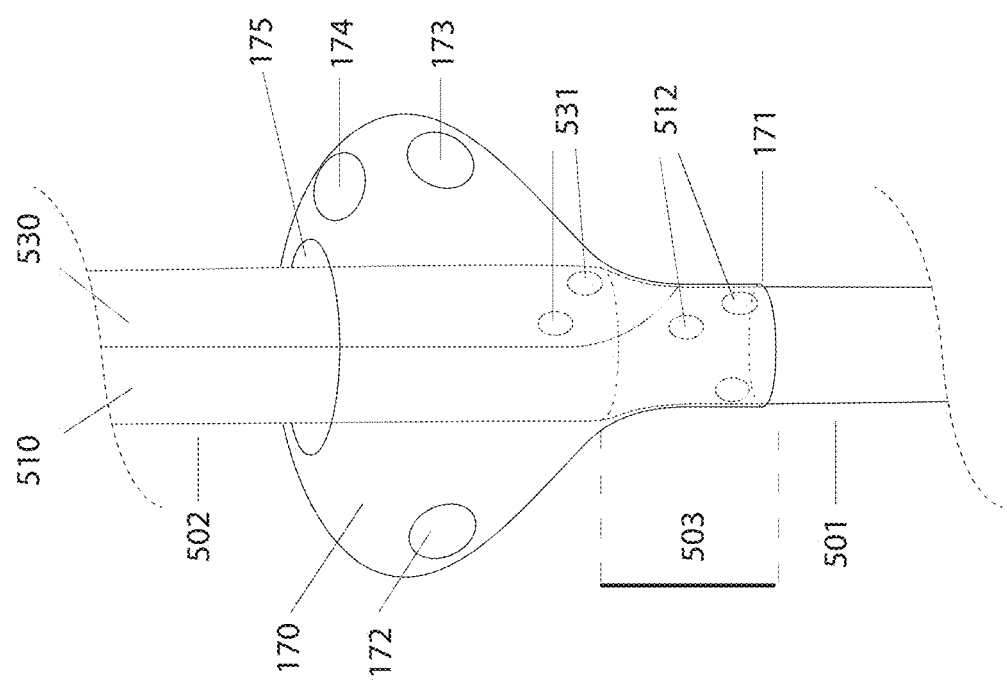

With reference to FIGS. 1A-B, 3, 9A, and 13A-B, the DST 500 can be used with an airway mask that has a gastric-pharyngeal access channel 150 with or without the pharyngeal suction channel 140. For embodiments (e.g. airway device 30 shown in FIG. 3) devoid of the pharyngeal suction channel 140, the ampulla-pharyngeal drains can only be accessed through the gastric-pharyngeal access channel 150. The DST 500 can be placed through the gastric-pharyngeal access channel via the proximal opening 151 located near the mask-airway channel junction 13. The lower section 501 can pass through the oval-shaped gastric-pharyngeal access channel 150 and the funnel-shaped distal port 171 of the ampulla, entering the stomach via the esophagus, until the cone-shaped transitional zone 503 reaches the funnel-shaped distal port 171 of the ampulla where the DST is prevented from being further inserted (FIGS. 13A and 14C). That is, the DST 500 can be configured and/or dimensioned to be inserted into the mask portion via the gastric-pharyngeal channel until the transitional zone engages the distal port 171 of the ampulla, which is configured and dimensioned to engage and stop the advancement of the dual suction tube 500. At this position, the distal gastric eyelets 511 are positioned in the stomach approximately 15 cm below the gastro-esophageal junction, while the pharyngeal eyelets 531 of the pharyngeal lumen are positioned above the funnel-shaped distal port inside the ampulla 170 (FIGS. 13A and 14C). For embodiments of DST 500 that include the proximal eyelets 512 of the gastric lumen, in this position, the proximal eyelets 512 of the gastric lumen are blocked in the funnel-shaped distal port 171 of the ampulla (FIG. 13A). Suction of the stomach is achieved if the vacuum is connected to the proximal port 513 of gastric lumen 510, while suction of the ampulla-pharyngeal drains is achieved if vacuum is applied to the proximal port 533 of the pharyngeal lumen 530. If the pharyngeal eyelets 531 are clogged, the DST 500 may be pulled back by 5 to 8 mm to position the proximal eyelets 512 of the gastric lumen in the ampulla for evacuation of the ampulla-pharyngeal drains (FIG. 13B).

FIG. 9B is a cross-sectional view of the upper section 502 of the DST 500 shown in FIG. 9A. As shown in FIG. 9B, DST 500 includes three lumens: the gastric lumen 510; the air lumen 520; and the pharyngeal lumen 530. The DST 500 can have a generally oval or elliptical cross-sectional shape defined by the gastric lumen 510 and the pharyngeal lumen 530, where the cross-sectional area of the gastric lumen 510 is larger than the cross-sectional area of the pharyngeal lumen 530. The adjacent sides of the gastric lumen 510 and the pharyngeal lumen 530 can be generally planer or linear, but can be reversible deformed during use. The air lumen 520 can be disposed within the gastric lumen 510 and can have a circular cross-section shape.

FIG. 9C is a cross-sectional view of the lower section 501 of the DST 500 shown in FIG. 9A. As shown in FIG. 9C, the lower section 501 in DST 500 can have a generally circular cross-sectional shape defined by the gastric lumen 510, which can have a generally tubular structure. The air lumen 520 can be disposed within the gastric lumen 510 and can have a circular cross-section shape.

Figure 14A:
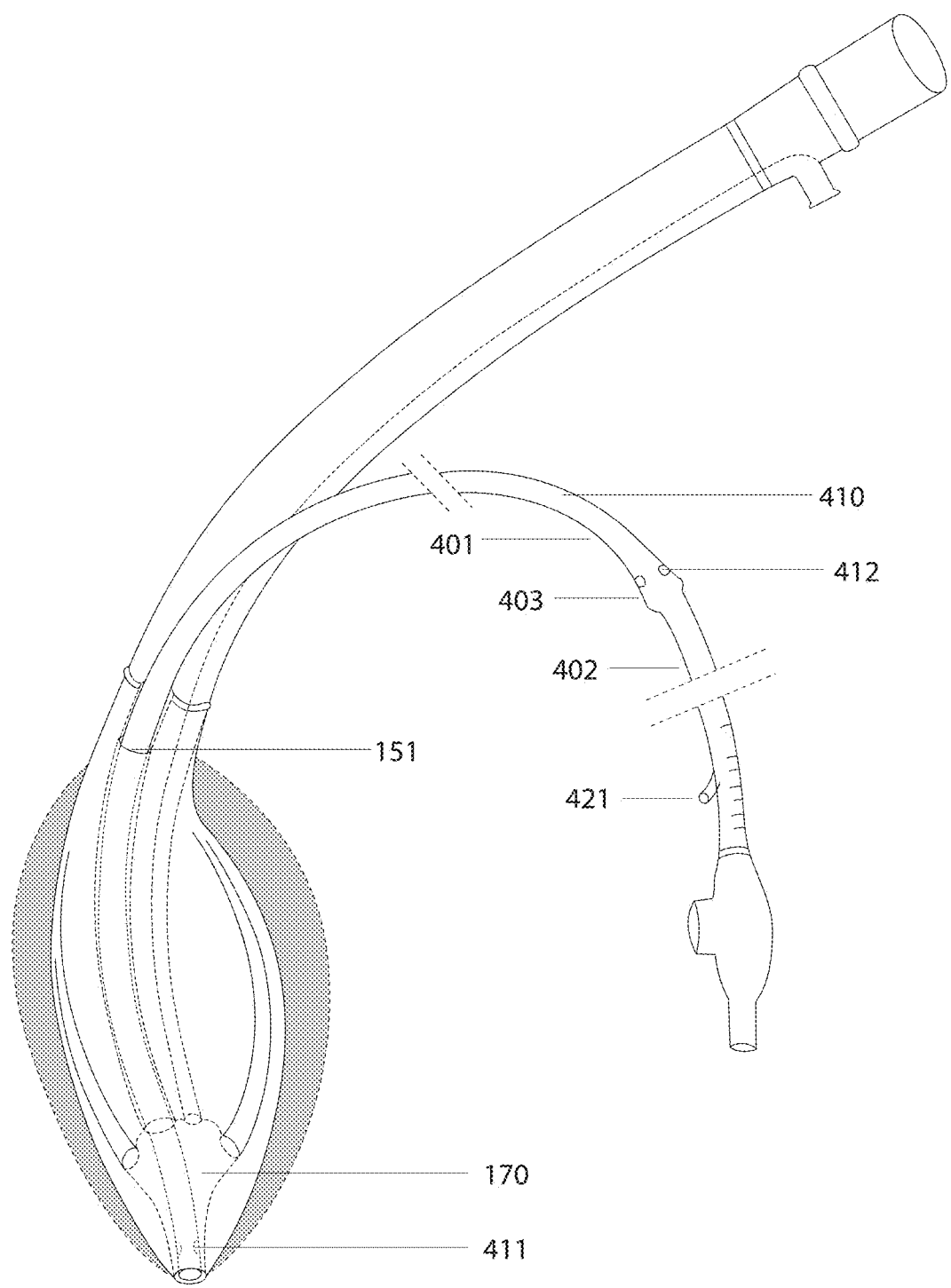
FIG. 14A illustrates an assembled system of an embodiment of the multi-channel flexible laryngeal mask airway device of FIG. 1A with a distal end of an embodiment of the DST of FIGS. 8A-B positioned within an ampulla of the airway device according to embodiments of the present disclosure.
Figure 14B:
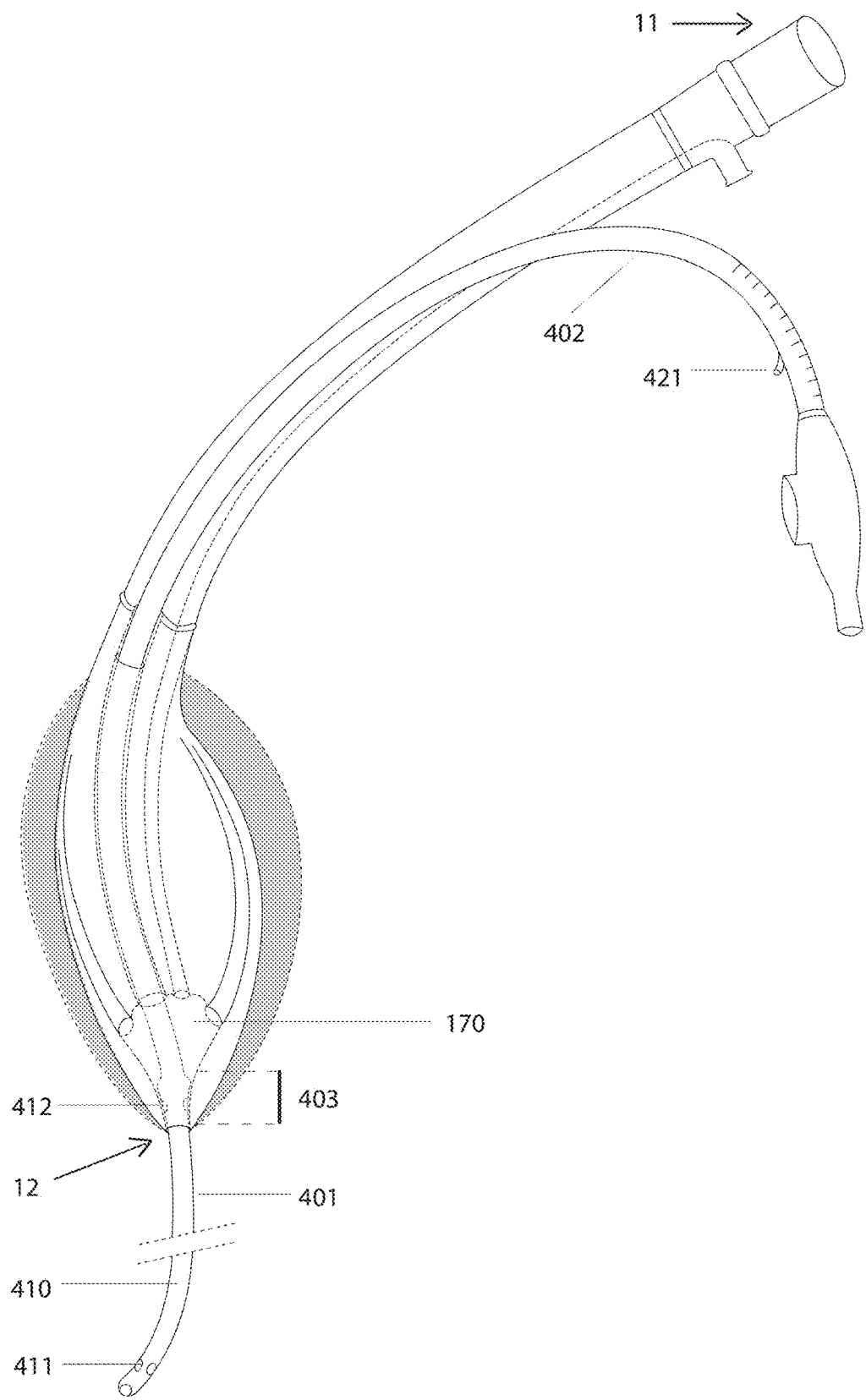
FIG. 14B illustrates the assembled system of FIG. 14A showing the transition zone of the DST engaging a funnel-shaped distal port of the ampulla, as in FIG. 12A, according to embodiments of the present disclosure.
Figure 14C:
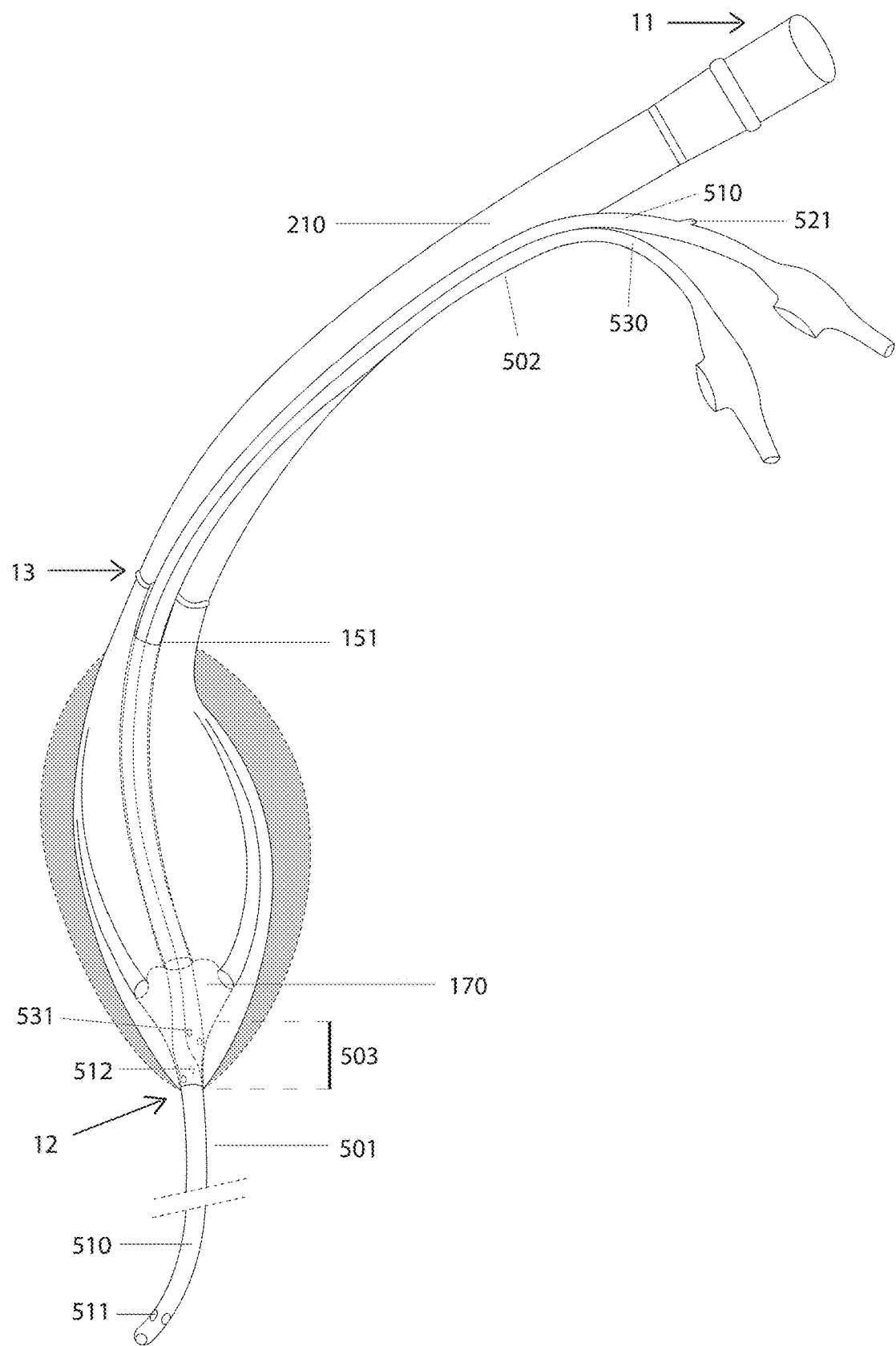
FIG. 14C illustrates an assembled system of an embodiment of the multi-channel flexible laryngeal mask airway device of FIG. 3 showing the transition zone of the DST engaging a funnel-shaped distal port of the ampulla, as in FIG. 13A, according to embodiments of the present disclosure.

FIGS. 14A-B illustrate an assembly of a multi-channel flexible laryngeal mask airway device system including an embodiment of the airway device 10 of FIG. 1A with an embodiment of the DST 400 of FIG. 8A-B. While FIGS. 14A-B illustrate a system including the airway device 10 and the DST 400, exemplary embodiments of systems in accordance with the present disclosure can be formed using any one of the airway devices 10, 10', or 30 with anyone of the DST 400 or 500 described herein. In FIG. 14A, the DST 400 is placed inside the gastric-pharyngeal access channel 150 through the proximal opening 151 (guided by the ramp 152) with a tip of DST 400 (i.e., the distal end) positioned in the ampulla 170. The DST 400 is advanced through the gastric-pharyngeal access channel and the lower section 401 passes through the funnel-shaped distal port 171 of the ampulla 170, and in FIG. 14B, the DST 400 is inserted further through the gastric-pharyngeal access channel 150 until the cone-shaped transitional zone 403 engages the funnel-shaped distal port 171 of the ampulla (FIG. 12A). In this position, suction through the gastric eyelets 411 can be achieved, while the pharyngeal eyelets 412 are blocked by the sidewall of the distal port 171 and are non-functional (FIG. 12A). The DST 400 can be pulled back towards the proximal end to position the pharyngeal eyelets 412 in the ampulla so that the pharyngeal eyelets are no longer blocked by the distal port 171 (FIG. 12B). At this point, suction through the pharyngeal eyelets 412 can be achieved to evacuate the ampulla and pharyngeal drains 160.

FIG. 14C illustrates an assembly of a multi-channel flexible laryngeal mask airway device system including an embodiment of the airway device 30 of FIG. 3 with an embodiment of the DST 500 of FIG. 9A-C. While FIG. 14C illustrates a system including the airway device 30 and the DST 500, exemplary embodiments of systems in accordance with the present disclosure can be formed using any one of the airway devices 10, 10', or 30 with anyone of the DST 400 or 500 described herein. In FIG. 14C, the DST 500 is placed inside the gastric-pharyngeal access channel 150 through the proximal opening 151 (guided by the ramp 152) with a tip of DST 500 (i.e., the distal end) positioned in the ampulla 170 (FIGS. 13A and 14C). The DST 500 is advanced through the gastric-pharyngeal access channel and the lower section 501 passes through the funnel-shaped distal port 171 of the ampulla 170. The DST 500 is inserted further through the gastric-pharyngeal access channel 150 until the cone-shaped transitional zone 503 engages the funnel-shaped distal port 171 of the ampulla 170 (FIGS. 13A and 14C). In this position, suction through the gastric eyelets 511 can be achieved and suction through the pharyngeal eyelets 531 can be achieved, while the pharyngeal eyelets 512 are blocked by the sidewall of the distal port 171 and are non-functional (FIG. 13A). The DST 500 can be pulled back towards the proximal end to position the pharyngeal eyelets 412 in the ampulla so that the pharyngeal eyelets 512 are no longer blocked by the distal port 171 (FIG. 13B). At this point, suction through the pharyngeal eyelets 512 can be achieved to evacuate the ampulla and pharyngeal drains 160.

FIG. 15 illustrates, according to the present disclosure, a perspective view of an exemplary multi-channel flexible laryngeal mask airway device 10 placed in the hypopharynx of a human with the mask covering the glottis and the airway channel extending outside the mouth. While FIG. 15 illustrates a system including the airway device 10 and the DST 400, exemplary embodiments of systems in accordance with the present disclosure can be formed using any one of the airway devices 10, 10', or 30 with anyone of the DST 400 or 500 described herein. An exemplary embodiment of the DST 400 is placed through the gastric-pharyngeal access channel 150 of the airway device into the human's esophagus and stomach with the distal part and gastric eyelets 411 of the lower section 401 in the stomach while its proximal end extends outside the mouth.

Figure 16:
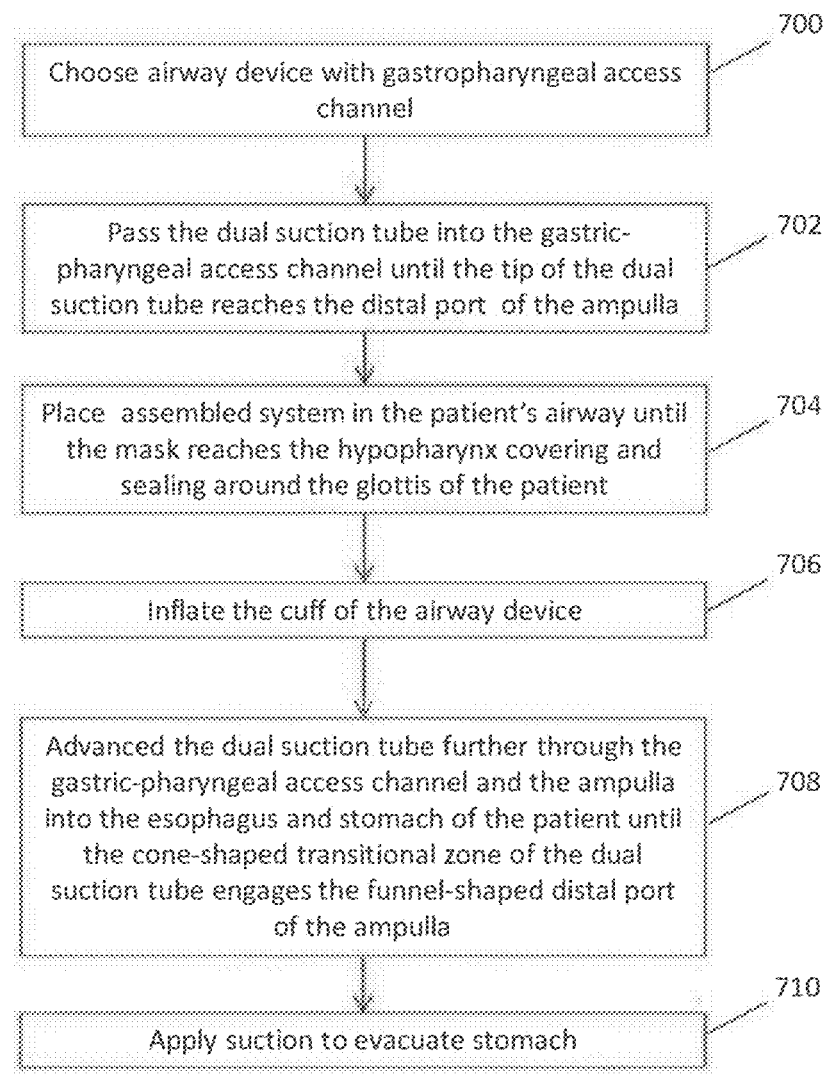
FIG. 16 illustrates a process of forming and using a system that includes an embodiment of the airway device of FIG. 1A, 1B, or 3, respectively and an embodiment of the dual suction tube of FIG. 8A-B or 9A-C, respectively.

FIG. 16 illustrates a general and common process of forming and using a system that includes an embodiment of the airway device 10, 10', or 30 of FIGS. 1A, 1B, and 3, respectively and an embodiment of the dual suction tube (DST) 400 or 500 of FIGS. 8 and 9, respectively. At the first step 700, airway device with a gastropharyngeal access channel is chosen. At step 702, the system is assembled before being placed in a patient by passing the DST with lubrication into the gastric-pharyngeal access channel 150 via its proximal opening 151 until the tip of the DST reaches the valve 176 of the distal port 171 of the ampulla 170. At step 704, after induction of general anesthesia, the assembly of the airway device and the DST is placed in the patient's airway until the mask reaches the hypopharynx covering and sealing around the glottis of the patient. A supporting arm may be used to facilitate the insertion of the airway device. At step 706, for embodiments of the airway device that include a cuff, the cuff is inflated if needed to achieve optimal seal.

At step 708, before or immediately after initiation of positive ventilation, the DST is advanced further through the gastric-pharyngeal access channel, the ampulla and the distal port and its valve into the esophagus and stomach of the patient until resistance is met, that is, until the cone-shaped transitional zone of the DST engages the funnel-shaped distal port 171 of the ampulla. The engagement between the transitional zone and the funnel-shaped distal port can provide a relatively secure position for the DST, while an easy passage of the DST generally indicates adequate placement of the airway device. At this point, the DST 400 or 500 is in fluid communication with the stomach through the gastric eyelets of the gastric lumen. At step 710, suction is applied to evacuate the stomach through the DST using vacuum to the proximal end of the gastric lumen. Adequate placement and effective ventilation via the airway device should be confirmed using the conventional method such as assessing airway compliance, minimal leak pressure, and the capnography waveform. Visual confirmation with a flexible bronchoscope through the airway channel may be used if indicated. If the seal is inadequate, a small amount of air is added to the cuff to achieve optimal seal; otherwise, the airway device is removed and replaced. During ventilation, air leak from the airway device into the stomach may be vented through the DST, preventing gastric insufflation. Gastric regurgitation may be monitored and evacuated through the DST as well. Further and subsequent steps should be followed and are described in the following paragraphs.

After evacuation of residual gastric fluid or content with suction through the gastric lumen, the DST can be left in place or removed, depending on the airway device used and clinical indications. For airway device 30, which has the gastric-pharyngeal access channel 150 but no pharyngeal suction channel 140, the DST should be kept in place for evacuation of the ampulla-pharyngeal drains through the pharyngeal eyelets of the DST as described herein. However, for airway device 10 or 10', which has the gastric-pharyngeal access channel 150 and the pharyngeal suction channel 140, the DST can be left in place for further monitoring and evacuation of gastric fluid during the surgery, and for evacuation of ampulla-pharyngeal drains as a back-up system for the pharyngeal suction channel 140; or the DST can be removed if there is no further indication or need for monitoring and evacuation of gastric fluid. Once the DST is removed, the tri-leaflets valve of the distal port can block or retard the fluid flowing from the ampulla into the esophagus while still allowing for air vent out of the esophagus-stomach, and the ampulla-pharyngeal drains can be accessed and evacuated through the pharyngeal suction channel 140. Removing the DST allows more space for surgical access to the oral cavity which may benefit surgical access to the oral airway.

If the dual section tube (DST) 400 is being used, the suction lumen 410 is separated from (i.e., not in fluid communication with) the ampulla-pharyngeal drains because the pharyngeal eyelets 412 in the cone-shaped transitional zone are blocked by the sidewall of the distal port 171 (FIG. 12A). The DST 400 can be backed out approximately 8 mm of the airway device to place the pharyngeal eyelets 412 in the ampulla so that the suction lumen is in fluid communication with the ampulla and the pharyngeal eyelets can be used to evacuate fluids from the ampulla (FIG. 12B). If, however, the DST 500 is being used, the pharyngeal eyelets 531 of the pharyngeal lumen 530 are separately and independently in fluid communication with the ampulla such that evacuation of the stomach and the ampulla can occur independently and/or simultaneously when the transitional zone 503 of the DST 500 is engaged with the distal port 171 of the ampulla (FIGS. 13A and 14C). In the event that the pharyngeal eyelets 531 of the pharyngeal lumen 530 become clogged, the DST 500 can be backed out approximately 8 mm to place the pharyngeal eyelets 512 on the gastric lumen 510 in the ampulla to evacuate fluids from the ampulla (FIG. 13B). For embodiments (airway device 10 or 10') in which the airway device includes a pharyngeal suction channel 140, the ampulla can be evacuated via the pharyngeal suction channel 140 independent of the DST.

Figure 17:
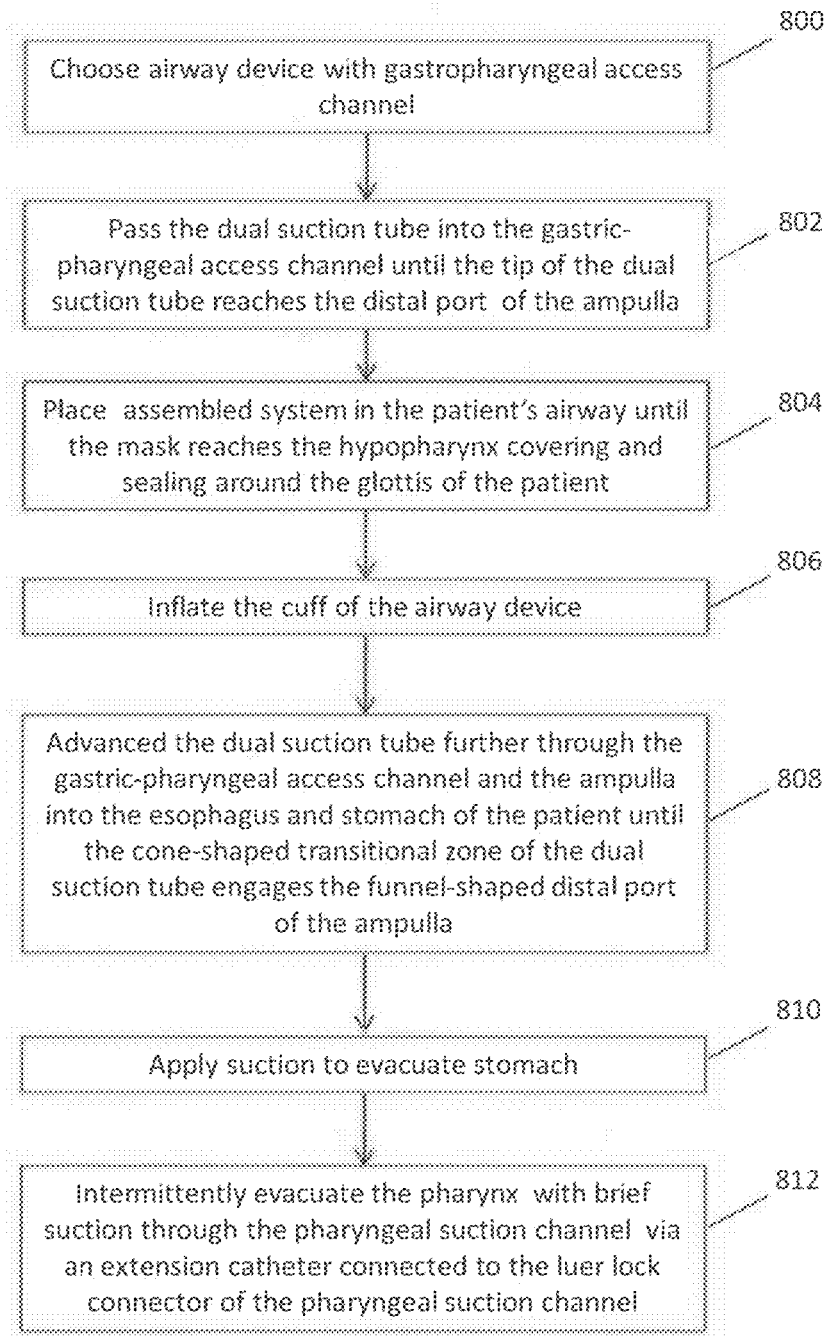
FIG. 17 illustrates a process of using a system including the laryngeal mask airway device of FIG. 1A, 1B, or 3, respectively, and an embodiment of the gastric-pharyngeal dual suction tube shown in FIGS. 8A-B.

FIG. 17 further illustrates a process of using a system including the laryngeal mask airway device 10 or 10' of FIG. 1, and an embodiment of the DST 400 shown in FIGS. 8A-B. At the first step 800, airway device with a gastropharyngeal access channel is chosen. At step 802, the system is assembled before being placed in a patient by passing the DST with lubrication into the gastric-pharyngeal access channel 150 via its proximal opening 151 until the tip of the DST reaches the distal port 171 of the ampulla 170. At step 804, after induction of general anesthesia, the assembly of the airway device and the DST is placed in the patient's airway until the mask reaches the hypopharynx covering and sealing around the glottis of the patient. A supporting arm may be used to facilitate the insertion of the airway device. At step 806, for embodiments of the airway device that include a cuff, the cuff is inflated if needed to achieve optimal seal.

At step 808, before or immediately after initiation of positive ventilation, the DST is advanced further through the gastric-pharyngeal access channel and the ampulla (including the distal port and its valve) into the esophagus and stomach of the patient until resistance is met, that is, until the cone-shaped transitional zone of the DST engages the funnel-shaped distal port 171 of the ampulla. The engagement between the transitional zone and the funnel-shaped distal port can provide a relatively secure position for the DST, while an easy passage of the DST generally indicates adequate placement of the airway device. At this point, the DST 400 or 500 is in fluid communication with the stomach through the gastric eyelets of the gastric lumen. At step 810, suction is applied to evacuate the stomach through the DST using vacuum to the proximal end of the gastric lumen. Adequate placement and effective ventilation via the airway device should be confirmed using the conventional method such as assessing airway compliance, minimal leak pressure, and the capnography waveform. Visual confirmation with a flexible bronchoscope through the airway channel may be used if indicated. If the seal is inadequate, a small amount of air is added to the cuff to achieve optimal seal; otherwise, the airway device is removed and replaced. During ventilation, air leak from the airway device into the stomach may be vented through the DST, preventing gastric insufflation. Gastric regurgitation may be monitored and evacuated through the DST as well. Further and subsequent steps should be followed and are described in the following paragraphs.

At step 812, during the surgery and upon the onset of active surgical bleeding, blood as well as secretions and surgical debris in the pharynx is intermittently evacuated with brief suction through the pharyngeal suction channel 140 via an extension catheter 145 connected to the female luer lock connector 142 of the pharyngeal suction channel. The frequency of suction may vary, depending on the amount of surgical bleeding, with the goal of preventing blood accumulation in the pharynx while also avoiding potential injury to the mucosa by continuous suction. As atmospheric air may be drawn into the system through the pharyngeal drains as well as the gastric-pharyngeal access channel, the risk of vacuum injury to the mucosa is minimized. The DST should effectively block or retard the drainage of blood from the ampulla into the esophagus, ensuring effective evacuation of blood from the pharynx through the pharyngeal suction system and preventing blood irritation to the stomach and subsequent nausea or vomiting after the surgery. If the pharyngeal suction channel 140 ceases to function properly, it can be flushed with a small amount of saline using a syringe attached to the female luer lock connector 142 to clear the blockage. Otherwise, the DST 400 can be withdrawn slightly from the airway device to unseal the pharyngeal eyelets 412 (as shown in FIG. 12B) and to facilitate evacuation of blood or other fluids in the ampulla through the pharyngeal eyelets of the DST 400. During emergence from anesthesia, the operating table can be placed in a back-up position with the patient's head raised to facilitate drainage of postnasal blood and to better support spontaneous respiration. The DST 400 can be removed while being under vacuum suction. Subsequently, frequent suction is applied to the pharyngeal suction catheter 141 to remove residual blood or continuous oozing and secretions. When the patient is able to open his/her mouth on command, the airway device is removed without cuff deflation and with continuous suction applied to the pharyngeal suction catheter. This would clear the residual blood and secretions in the upper airway as the airway device is being removed, further preventing irritation of the airway and the glottis.

Figure 18:
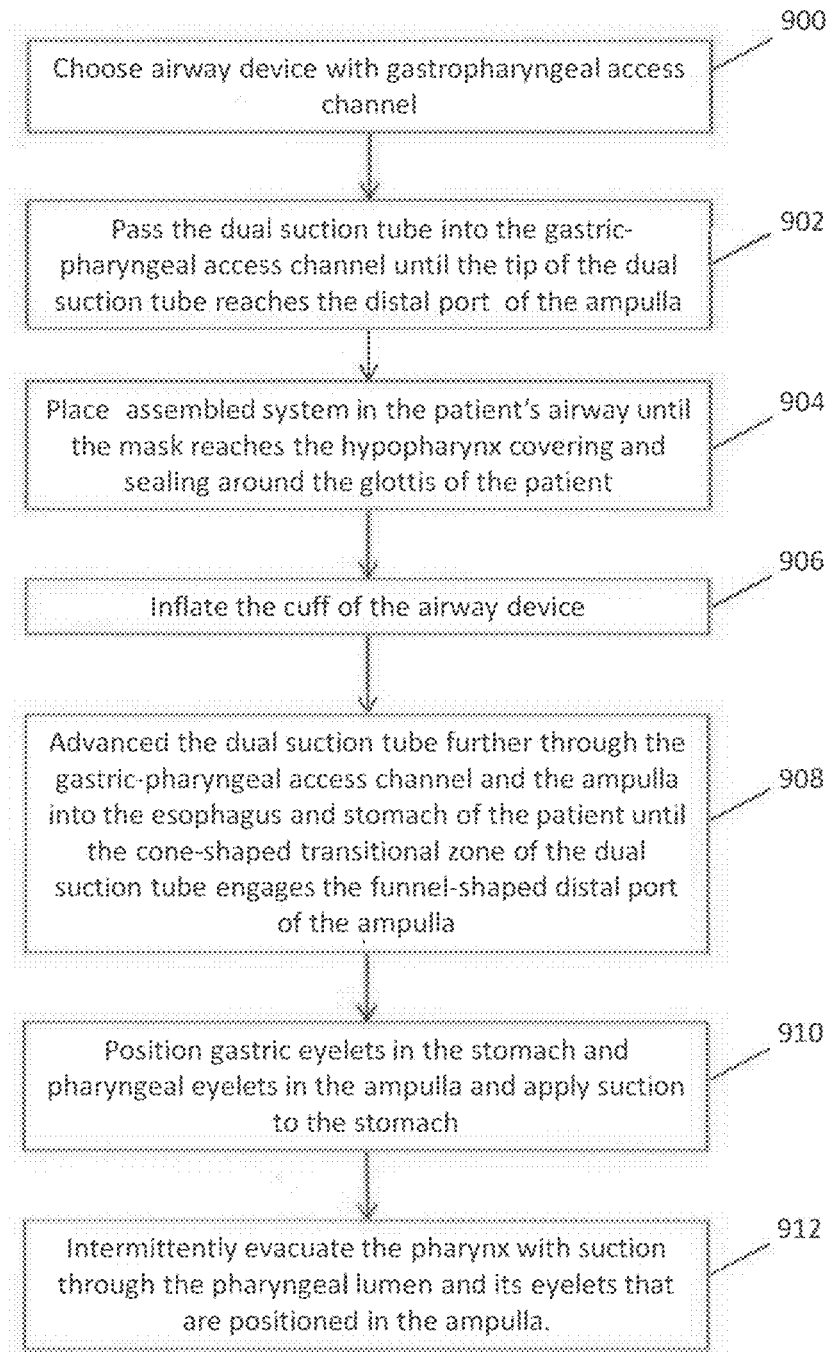
FIG. 18 illustrates a process of using a system including the laryngeal mask airway device of FIG. 1A, 1B, or 3, respectively, and an embodiment of the gastric-pharyngeal dual suction tube shown in FIGS. 9A-C

FIG. 18 illustrates a process of using a system including the laryngeal mask airway device 30 of FIG. 3, which has no pharyngeal suction channel 140, and an embodiment of the DST 500 of FIG. 9. At the first step 900, airway device with a gastropharyngeal access channel is chosen. At step 902, the system is assembled before being placed in a patient by passing the DST with lubrication into the gastric-pharyngeal access channel 150 via its proximal opening 151 until the tip of the DST reaches the distal port 171 of the ampulla 170. At step 904, after induction of general anesthesia, the assembly of the airway device and the DST is placed in the patient's airway until the mask reaches the hypopharynx covering and sealing around the glottis of the patient. A supporting arm may be used to facilitate the insertion of the airway device. At step 906, for embodiments of the airway device that include a cuff, the cuff is inflated if needed to achieve optimal seal. At step 908, before or immediately after initiation of positive ventilation, the DST is advanced further through the gastric-pharyngeal access channel and the ampulla into the esophagus and stomach of the patient until resistance is met, that is, until the cone-shaped transitional zone of the DST engages the funnel-shaped distal port 171 of the ampulla.

At step 910, when the transitional zone 503 is engaged with the distal port 171 of the ampulla, the DST 500 is in fluid communication with the stomach through its gastric lumen 510 and gastric eyelets 511, and also in fluid communication with ampulla-pharyngeal drains through the pharyngeal lumen 530 and the eyelets 531 that are located above the transitional zone and positioned in the ampulla (as shown in FIGS. 13A and 14C), apply suction to the gastric lumen to evacuate the stomach. At step 912, during the surgery and upon the onset of active surgical bleeding, blood as well as secretions and surgical debris in the pharynx can be intermittently evacuated with brief suction through the pharyngeal lumen 530 and the eyelets 531 that are positioned in the ampulla, since airway device 30 has no pharyngeal suction channel 140. The frequency of suction may vary, depending on the amount of surgical bleeding, with the goal of preventing blood accumulation in the pharynx while also avoiding potential injury to the mucosa. As atmospheric air may be drawn into the system through the pharyngeal drains as well as the gastric-pharyngeal access channel, the risk of vacuum injury to the mucosa is minimized. The transitional zone should effectively block or retard the drainage of blood from the ampulla into the esophagus, ensuring effective evacuation of blood from the pharynx through the pharyngeal lumen 530 and preventing blood irritation to the stomach and subsequent nausea or vomiting after the surgery. If the pharyngeal lumen 530 is clogged during the surgery, the DST 500 can be withdrawn from the airway device about five (5) to eight (8) millimeters to unseal the proximal eyelets 512 of the gastric lumen 510 (as shown in FIG. 13B), which may be then used to evacuate the pharynx via the ampulla-pharyngeal drain system. During emergence from anesthesia, the operating table is placed in a back-up position with the patient's head raised to facilitate drainage of postnasal blood and to better support spontaneous respiration. Frequent suction is applied to the pharyngeal lumen of the DST 500 to remove residual blood or continuous oozing and secretions. When the patient is able to open his/her mouth on command, the DST 500 is removed with continuous suction applied to the pharyngeal lumen via its proximal three-way port 533, followed by the removal of the airway device without cuff deflation.

Unlike airway devices 10, 10', and 30, the airway devices 20 and 20' can and should be used alone, and cannot be used with the DST since they do not have a gastropharyngeal access channel to accommodate the DST. In an exemplary application, referring to FIGS. 2A-B, the airway device 20 or 20' can be inserted into the upper airway with the mask portion 100 covering the glottis, and with the airway channel 210 and the pharyngeal suction channel 140 extending outside of a mouth of the patient. The airway device 20 or 20' can allow access to the upper airway of the human for surgeries or procedures involving the upper airway while proving ventilation of lungs through the mask and the flexible thin airway channel. During positive ventilation, the tri-leaflet valve 176 of the distal port allows air vent out of the esophagus and stomach, preventing gastric insufflation due to air leaking from the airway through the mask. Upon the onset of active surgical bleeding, blood as well as secretions and surgical debris in the pharynx is collected via the pharyngeal drains-ampulla and can be evacuated with intermittent suction through the pharyngeal suction channel 140 connected via an upper port 174 to the ampulla. The frequency of suction may vary, depending on the amount of surgical bleeding, with the goal of preventing blood accumulation in the pharynx while also avoiding potential injury to the mucosa from continuous suction. As atmospheric air may be drawn into the system through the pharyngeal drains, the risk of vacuum injury to the mucosa is minimized. The tri-leaflet valve 176 of the distal port blocks or retards the drainage of blood and/or secretions from the ampulla into the esophagus, ensuring effective evacuation of blood from the pharynx through the pharyngeal suction channel and preventing blood irritation to the stomach and subsequent nausea or vomiting after the surgery. If the pharyngeal suction channel is clogged during surgery, the suction system can be flushed with saline using a syringe attached to the female luer lock connector 142. During emergence from anesthesia, the operating table is placed in a back-up position with the patient's head raised to facilitate drainage of postnasal blood and to better support spontaneous respiration. Frequent suction is applied to the pharyngeal suction catheter to remove residual blood or continuous oozing and secretions. When the patient is able to open his/her mouth on command, the airway device is removed, without cuff deflation, while being under suction through the pharyngeal suction catheter.

Figure 19A:
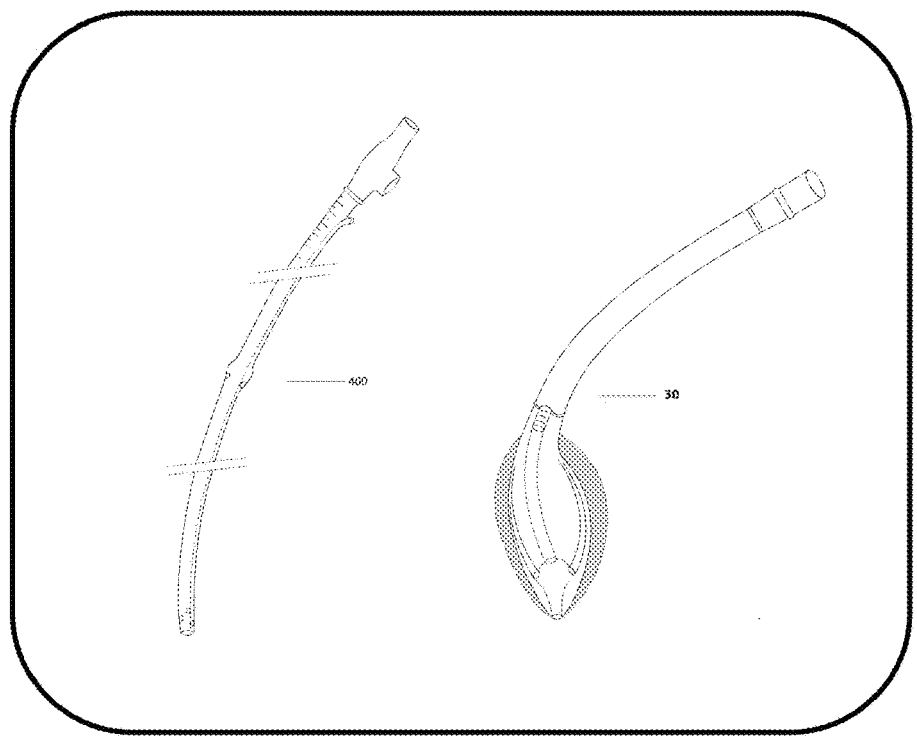
FIG. 19A-H illustrates various kits that can be formed in accordance with embodiments of the present disclosure.
Figure 19B:
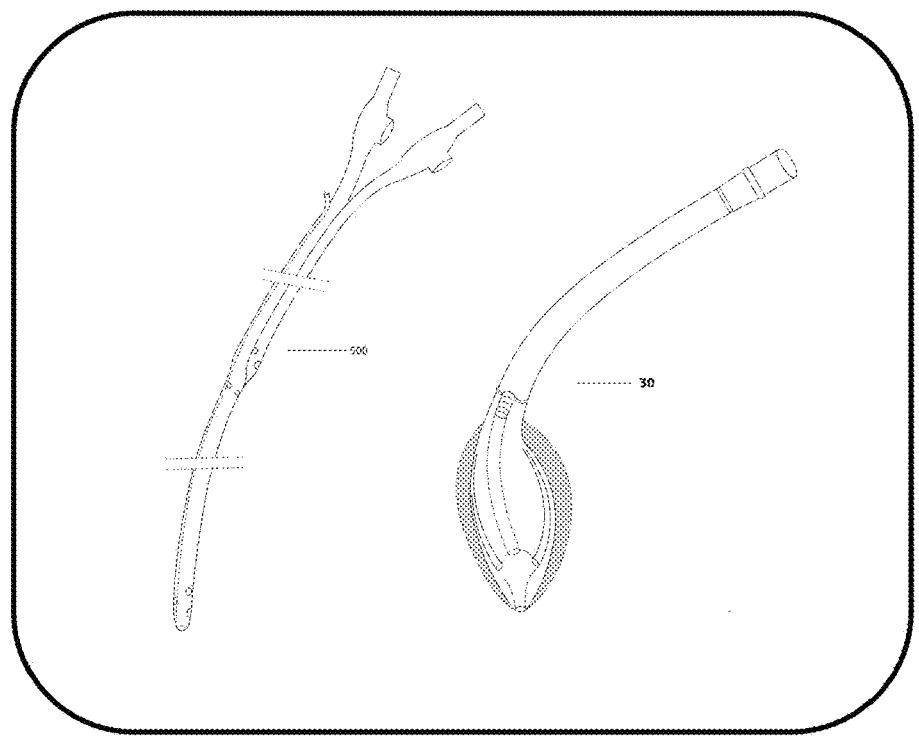
Figure 19C:
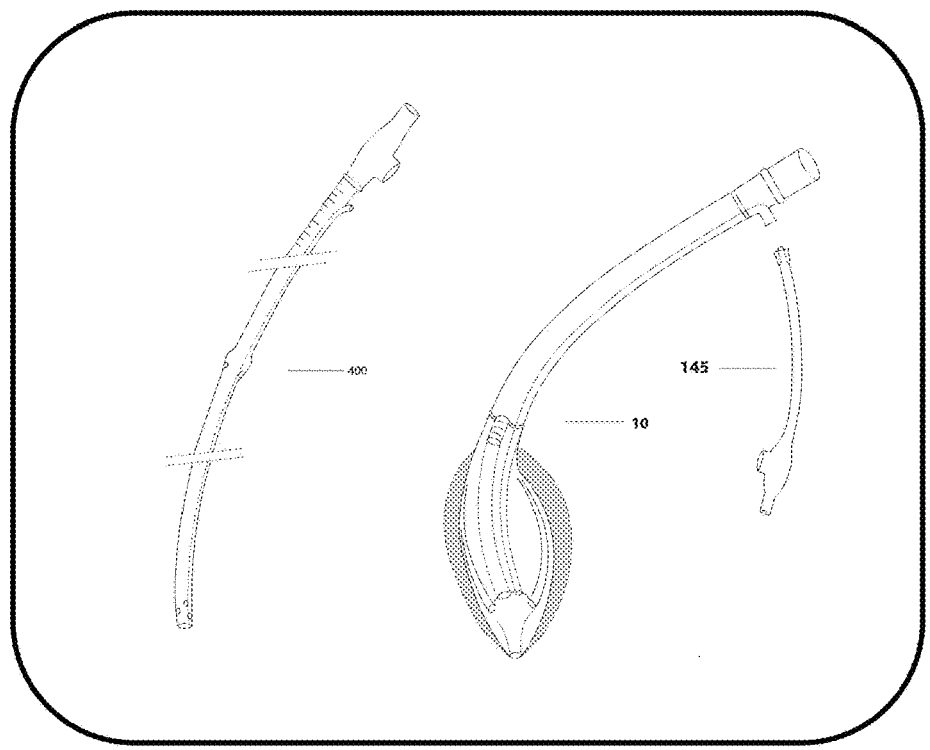
Figure 19D:
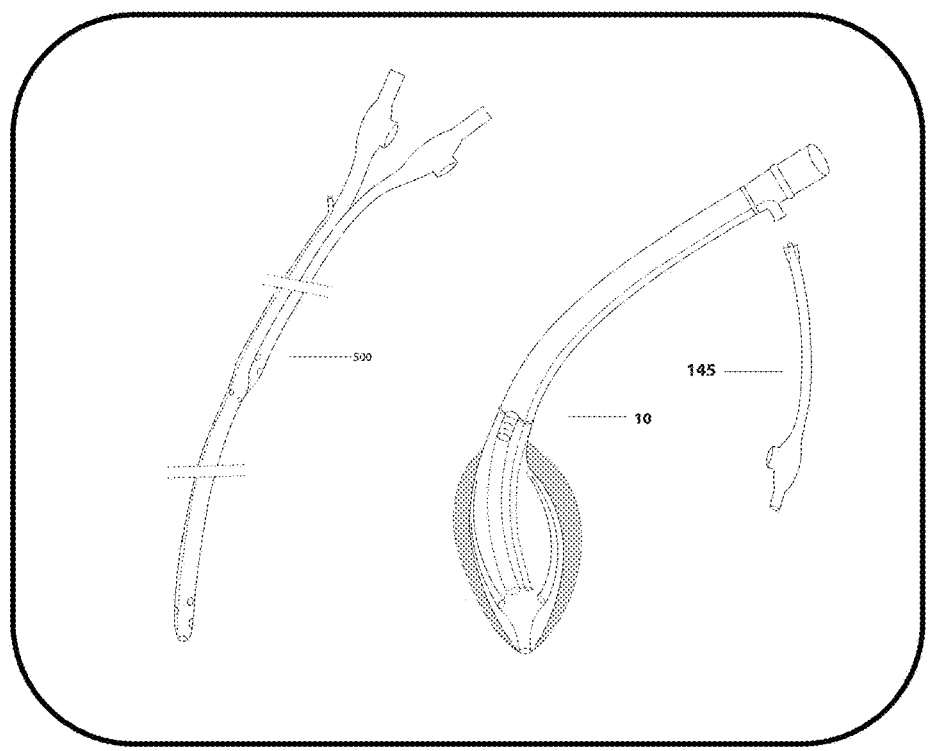
Figure 19E:
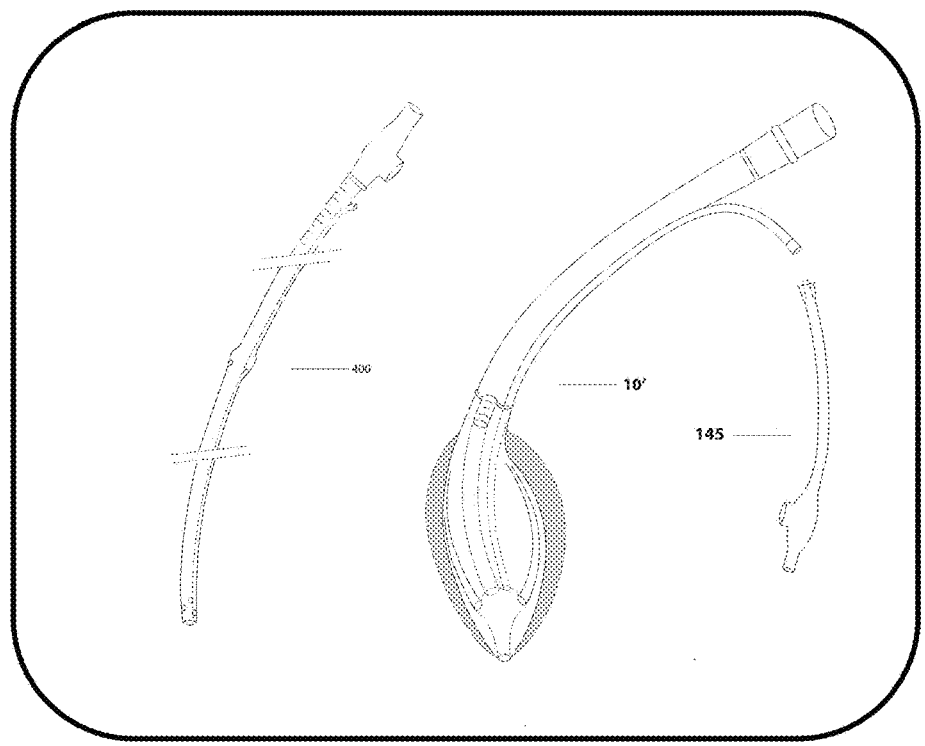
Figure 19F:
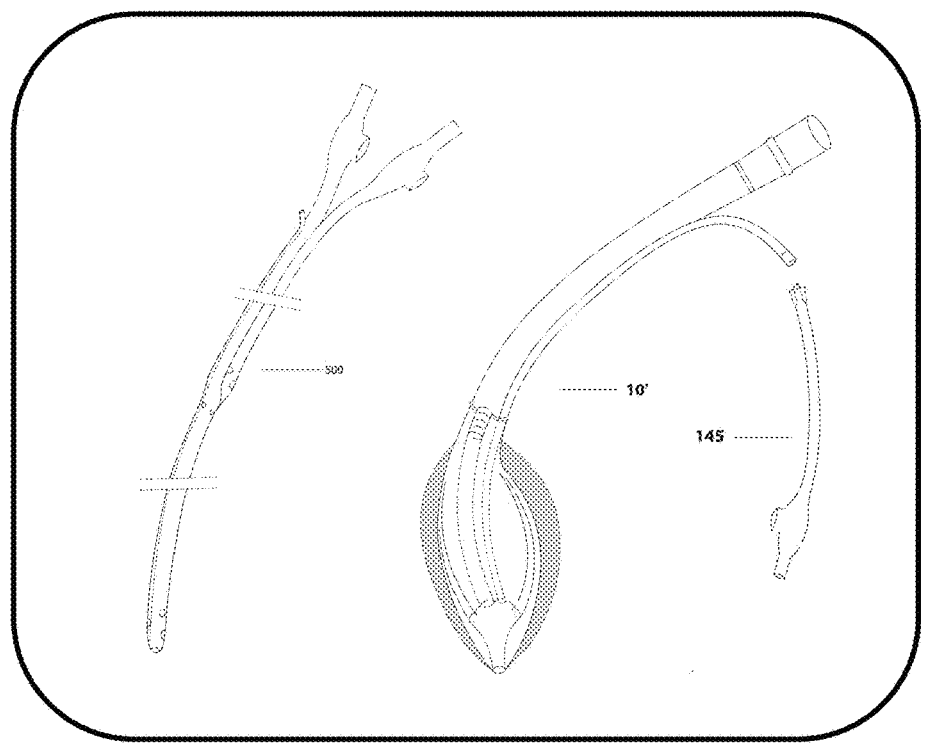
Figure 19:
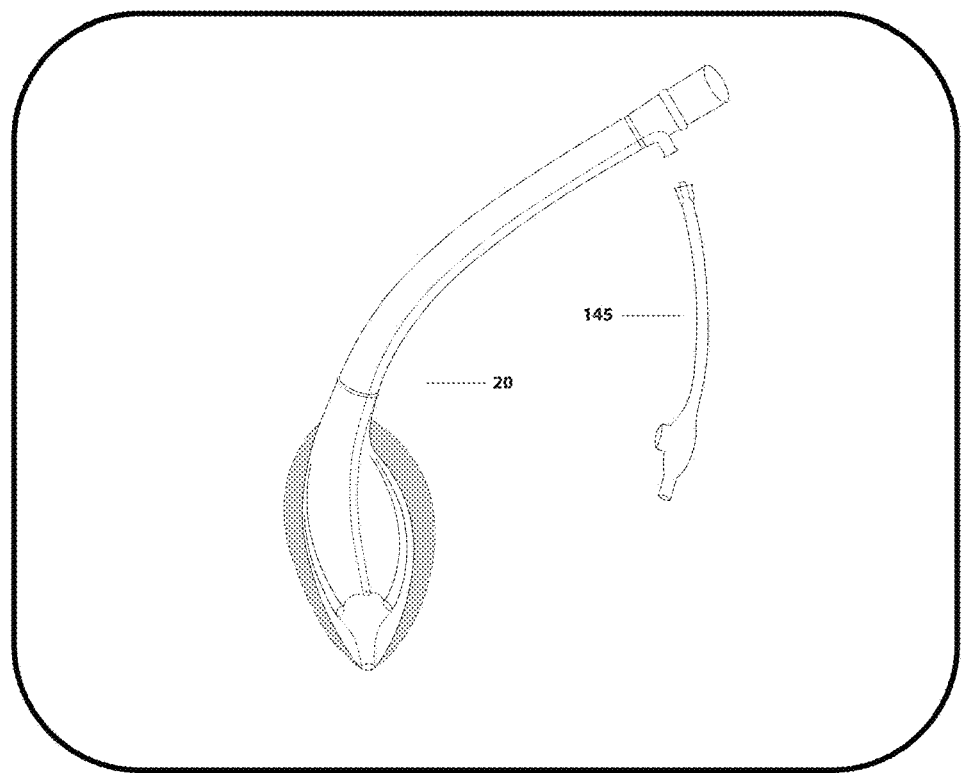
Figure 19H:
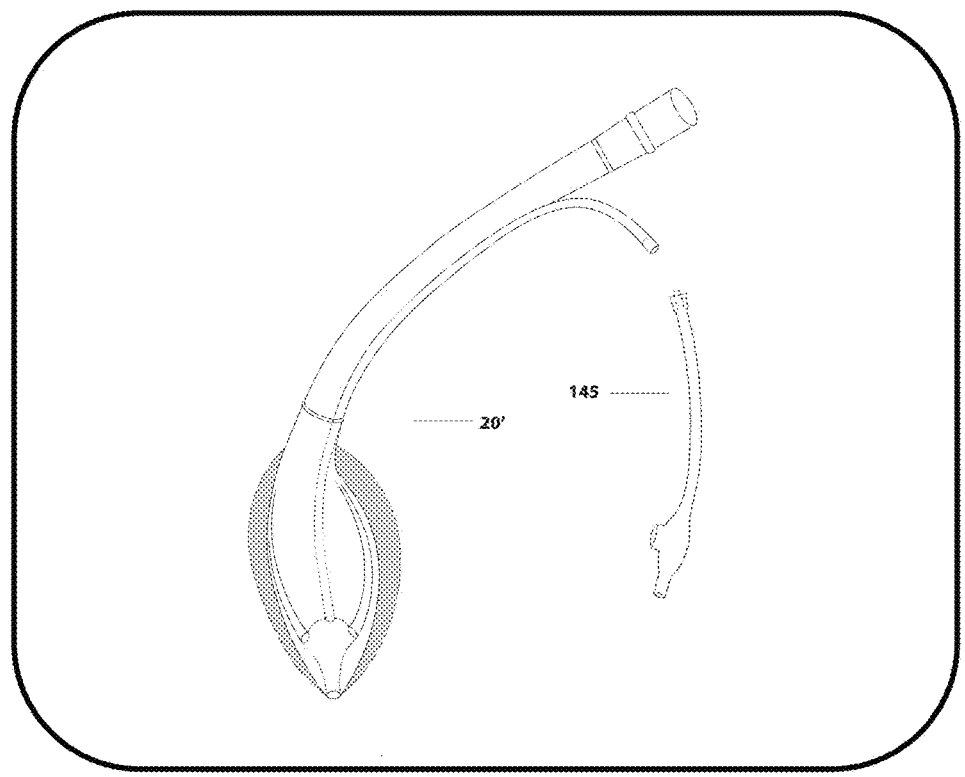

FIG. 19A-H illustrates various kits that can be formed in accordance with embodiments of the present disclosure. FIG. 19A illustrates a kit that includes the airway device 30 of FIG. 3 and the DST 400 of FIGS. 8A-B. FIG. 19B illustrates a kit that includes the airway device 30 of FIG. 3 and the DST 500 of FIGS. 9A-C. FIG. 19C illustrates a kit that includes the airway device 10 of FIG. 1A and the DST 400 of FIGS. 8A-B with or without the extension catheter 145. FIG. 19D illustrates a kit that includes the airway device 10 of FIG. 1A and the DST 500 of FIGS. 9A-C with or without the extension catheter 145. FIG. 19E illustrates a kit that includes the airway device 10' of FIG. 1B and the DST 400 of FIGS. 8A-B with or without the extension catheter 145. FIG. 19F illustrates a kit that includes the airway device 10' of FIG. 1B and the DST 500 of FIGS. 9A-C with or without the extension catheter 145. FIG. 19G illustrates a kit that includes the airway device 20 of FIG. 2A with or without the extension catheter 145. FIG. 19H illustrates a kit that includes the airway device 20' of FIG. 2B with or without the extension catheter 145.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The invention claimed is:

1. A laryngeal mask airway system, the system comprising:
   an airway channel portion including an airway channel; and
   a mask portion operatively coupled to the airway channel portion via an airway channel-mask junction, the mask portion including a mask, a gastric-pharyngeal access channel, and an ampulla, the ampulla is disposed proximate to a distal end on a back of the mask portion and includes a plurality of ports, wherein a first port of the plurality of ports is a largest one of the plurality of ports, the gastric-pharyngeal access channel extends upward within the back of the mask portion from the first port to an opening at which the gastric-pharyngeal access channel terminates on the back of the mask portion at a proximal end of the mask portion in proximity to the airway channel-mask junction.

2. The system of claim 1, further comprising a ramp on the mask sloping towards the opening of the gastric-pharyngeal access channel.

3. The system of claim 1, wherein a second port of the plurality of ports of the ampulla is oppposingly spaced from the first port and opens towards an esophagus of a human when the mask portion is placed in the hypopharynx of the human.

4. The system of claim 3, wherein a distal end of the second port includes a valve.

5. The system of claim 4, wherein the valve is formed by a plurality of leaflets.

6. The system of claim 4, wherein in a closed position, adjacent ones of the plurality of leaflets engage each other to form a center opening.

7. The system of claim 3, wherein the second port is a funnel-shape having first cross-sectional dimensions at the ampulla and second cross-sectional dimensions at a distal end of the second port.

8. The system of claim 7, wherein a first cross-sectional area of the second port at the ampulla is greater than the second cross-sectional area of the second port at the distal end of the second port.

9. The system of claim 8, wherein the gastric-pharyngeal access channel has a third cross-sectional area that is greater than the second cross-sectional area of the second port.

10. The system of claim 1, further comprising:
at least one pharyngeal drain formed on the mask, the at least one pharyngeal drain being operatively coupled to a third port of the plurality of ports of the ampulla.

11. The system of claim 1, further comprising:
a pharyngeal suction channel that extends from a proximal end of the airway channel portion to a fourth port of the plurality of ports of the ampulla.

12. The system of claim 11, wherein a first portion of the pharyngeal suction channel is formed within the airway channel and a second portion of the pharyngeal suction channel is formed within the mask.

13. The system of claim 11, wherein a first portion of the of the pharyngeal suction channel is formed outside the airway channel along the airway channel portion and a second portion of the pharyngeal suction channel is formed within the mask.

14. The system of claim 1, wherein the gastric-pharyngeal access channel has an oval cross-sectional shape.

15. The system of claim 1, further comprising:
a dual suction tube having a lower section, an upper section, and a transitional zone between the lower and upper sections.

16. The system of claim 15, wherein a distal end of the lower section includes at least one eyelet.

17. The system of claim 15, wherein the transitional zone includes at least one eyelet.

18. The system of claim 15, wherein a proximal end of the transitional zone is larger than a distal end of the transitional zone.

19. The system of claim 15, wherein a second port of the plurality of ports of the ampulla is oppposingly spaced from the first port and opens towards an esophagus of a human when the mask portion is placed in the hypopharynx of the human, and
wherein the lower section of the dual suction tube is configured and dimensioned to be inserted in and passed through the gastric-pharyngeal access channel, the first port, the ampulla, and the second port.

20. The system of claim 19, wherein the second port is a funnel-shape having first cross-sectional dimensions at the ampulla and second cross-sectional dimensions at a distal end of the second port, and
wherein the transitional zone is configured and dimensioned to be inserted in and passed through the gastric-pharyngeal access channel, the first port, and the ampulla, and the transitional zone is configured and dimensioned to engage the second port, which is configured and dimensioned to prevent the transitional zone from passing through,
wherein the dual suction tube is configured and/or dimensioned to be inserted into the mask portion via the gastric-pharyngeal channel until the transitional zone engages the second port of the ampulla and stops the advancement of the dual suction tube.

21. The system of claim 20, wherein the second port is configured and dimensioned to prevent the transitional zone from passing through the second port.

22. The system of claim 21, wherein the dual suction tube is configured and dimensioned to be inserted into the mask portion until the transitional zone engages the second port.

23. The system of claim 21, wherein at least one eyelet is disposed near the distal end of the transitional zone and the at least one eyelet is blocked when the transitional zone is engaged with the second port.

24. The system of claim 15, wherein the dual suction tube includes an inner lumen that forms an air vent.

25. The system of claim 15, wherein the dual suction tube includes a gastric lumen and a pharyngeal lumen.

26. The system of claim 15, wherein the gastric lumen extends a length of the dual suction tube and the pharyngeal lumen extends from a proximal end of the dual suction tube to the transitional zone.

27. The system of claim 15, wherein the pharyngeal lumen includes at least one eyelet disposed at a distal end of the pharyngeal lumen which is configured to be positioned in the ampulla when the dual suction tube is inserted into the mask portion and the transitional zone is engaged with the second port of the ampulla.

28. An airway system, the system comprising:
a laryngeal mask including:
an airway channel portion; and
a mask portion, the mask portion including a gastric-pharyngeal access channel and an ampulla,
the gastric-pharyngeal access channel extending upward within a back of the mask portion from a first port of the ampulla to an opening at which the gastric-pharyngeal access channel terminates on the back of the mask portion at a first end of the mask portion in proximity to an airway channel-mask junction,
the ampulla being disposed proximate to a second end on the back of the mask portion and including a second port that is oppposingly spaced relative to the first port, the second port being funnel-shaped, wherein the first port is greater than the second port; and a dual suction tube including:
- a lower section including at least one eyelet disposed at a distal end of the dual suction tube;
- an upper section including at least one port configured to be connected to a vacuum source; and
- a transitional zone disposed between the lower section and upper section, wherein the dual suction tube is configured and dimensioned to be inserted into the gastric-pharyngeal access channel passed the gastric-pharyngeal access channel, the first port, the ampulla into the second port until the transitional zone engages the second port which is configured and dimensioned to prevent the transitional zone from passing through the second port such that the dual suction tube is operable to evacuate fluids from a pharynx via the transition zone and to evacuate fluids from a stomach via the lower section when the mask portion is placed in the hypopharynx of the human.

29. The system of claim 28, wherein the transitional zone includes at least one eyelet and the at least one eyelet is blocked by the second port when the transitional zone engages the second port.

30. The system of claim 29, wherein the dual suction tube is configured to be withdrawn a specified distance from the mask portion to disengage the transitional zone from the second port and to align the at least one eyelet of the transitional zone with the ampulla to place the dual suction tube in fluid communication with the ampulla.

31. The system of claim 30, wherein the mask portion of the airway device includes pharyngeal drains formed on the mask, the pharyngeal drains being in fluid communication with the ampulla.

32. The system of claim 28, further comprising:
- a pharyngeal suction channel formed in the airway channel portion and the mask portion, wherein the pharyngeal suction channel includes a port at a proximal end of the laryngeal mask and terminates at a third port of the ampulla.

33. The system of claim 28, wherein the dual suction tube includes:
- a gastric lumen that extends a length of the dual suction tube; and
- a pharyngeal lumen that extends from a proximal end of the dual suction tube to the transitional zone.

34. The system of claim 33, wherein the pharyngeal lumen includes at least one eyelet disposed at a distal end of the pharyngeal lumen in proximity to the transitional zone.

* * * * *